(12) United States Patent
Ong et al.

(10) Patent No.: US 12,708,789 B2
(45) Date of Patent: Aug. 18, 2026

(54) FIXATION DEVICE WITH ELECTROMAGNETIC PUMP

(71) Applicant: University of Oregon, Eugene, OR (US)

(72) Inventors: Keat Ghee Ong, Eugene, OR (US); Robert Erling Guldberg, Eugene, OR (US); Eyerusalem A. Gebreyesus, Eugene, OR (US); Alice Park, Eugene, OR (US)

(73) Assignee: University of Oregon, Eugene, OR (US)

( * ) Notice: Subject to any disclaimer, the term of this patent is extended or adjusted under 35 U.S.C. 154(b) by 97 days.

(21) Appl. No.: 19/043,233

(22) Filed: Jan. 31, 2025

(65) Prior Publication Data

US 2025/0177767 A1 Jun. 5, 2025

Related U.S. Application Data

(63) Continuation of application No. PCT/US2023/029437, filed on Aug. 3, 2023.

(60) Provisional application No. 63/395,685, filed on Aug. 5, 2022.

(51) Int. Cl.

| | |
|---|---|
| ***A61M 99/00*** | (2012.01) |
| ***A61N 2/00*** | (2006.01) |
| ***A61N 2/02*** | (2006.01) |

(52) U.S. Cl.

CPC ............. *A61N 2/004* (2013.01); *A61M 99/00* (2022.08); *A61N 2/02* (2013.01); *A61M 2202/0405* (2013.01); *A61M 2205/04* (2013.01); *A61M 2210/02* (2013.01)

(58) Field of Classification Search

CPC ......... A61N 2/004; A61N 2/02; A61M 99/00; A61M 2202/0405; A61M 2205/04; A61M 2210/02

See application file for complete search history.

(56) References Cited

U.S. PATENT DOCUMENTS 5,000,178 A * 3/1991 Griffith .................... A61N 2/00 607/2
2007/0265682 A1 11/2007 Wiegmann et al.
2013/0153628 A1 6/2013 Euteneuer
2017/0245996 A1 8/2017 Nam et al.

(Continued)

OTHER PUBLICATIONS

Hakala et al., "Sampling of fluid through skin with magnetohydrodynamics for noninvasive glucose monitoring," Scientific Reports, 9 pp. (Apr. 2021).

(Continued)

*Primary Examiner* — Lindsey G Wehrheim
(74) *Attorney, Agent, or Firm* — Klarquist Sparkman, LLP

(57) ABSTRACT

An assembly for promoting interstitial fluid flow can include an implant having first and second electrodes, a control unit, and one or more magnets. The implant can be disposed at a selected site of a subject, and the control unit can be electrically coupled to the first and second electrodes and can provide power to the first and second electrodes to generate an electric field at the selected site. The one or more magnets can be disposed adjacent to the selected site and can generate magnetic field in a direction orthogonal to the electric field in order to drive electrically conductive interstitial fluid flow at the selected site.

20 Claims, 23 Drawing Sheets

(56) References Cited

U.S. PATENT DOCUMENTS

| | | | | |
|---|---|---|---|---|
| 2018/0221656 | A1 | 8/2018 | Garcia Perez et al. | |
| 2019/0175081 | A1 | 6/2019 | Garcia Perez et al. | |
| 2019/0255344 | A1* | 8/2019 | Carter | A61N 2/00 |

OTHER PUBLICATIONS

International Search Report and Written Opinion dated Nov. 6, 2023, from International Patent Application No. PCT/US2023/29437, 15 pp.

* cited by examiner 172
164
164
172
166
166
164
164

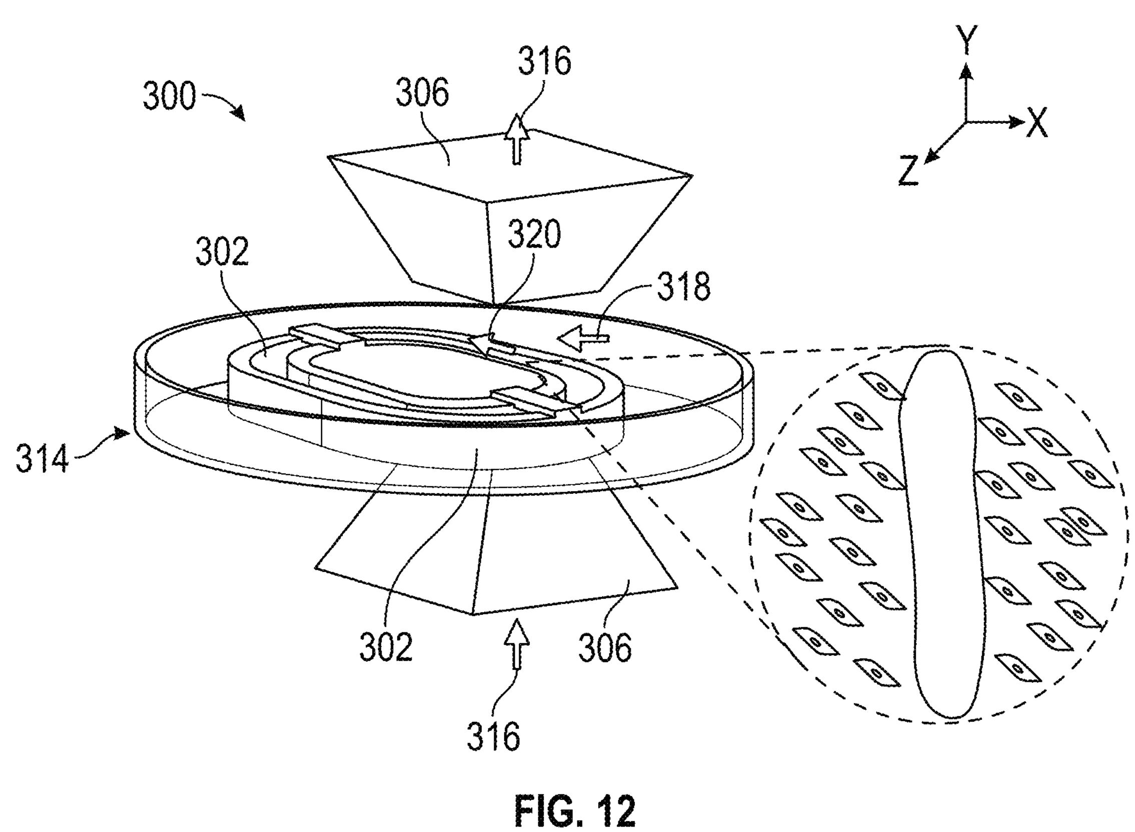
FIG. 12
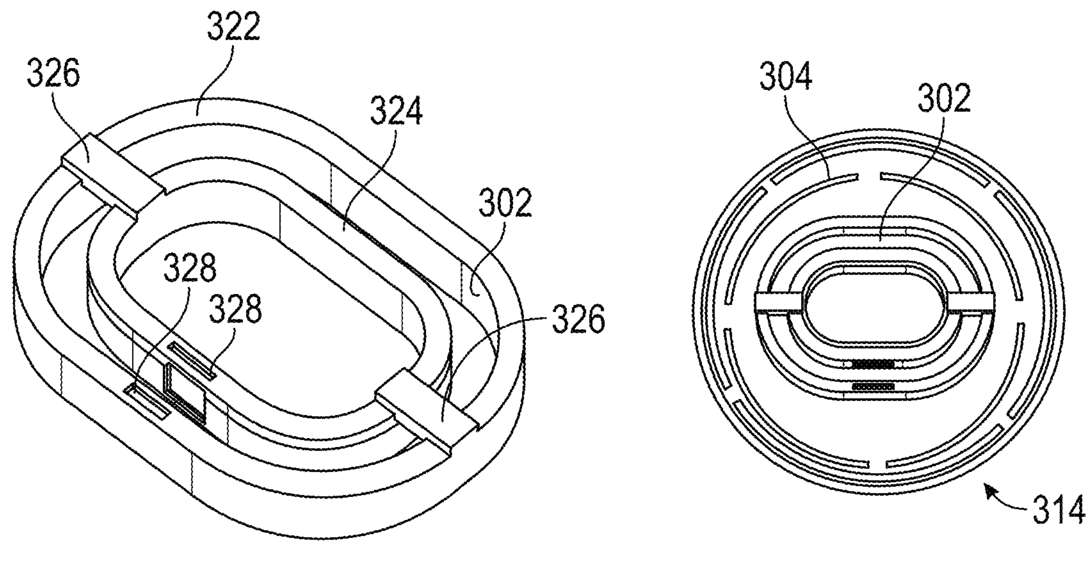
FIG. 13A
FIG. 13B

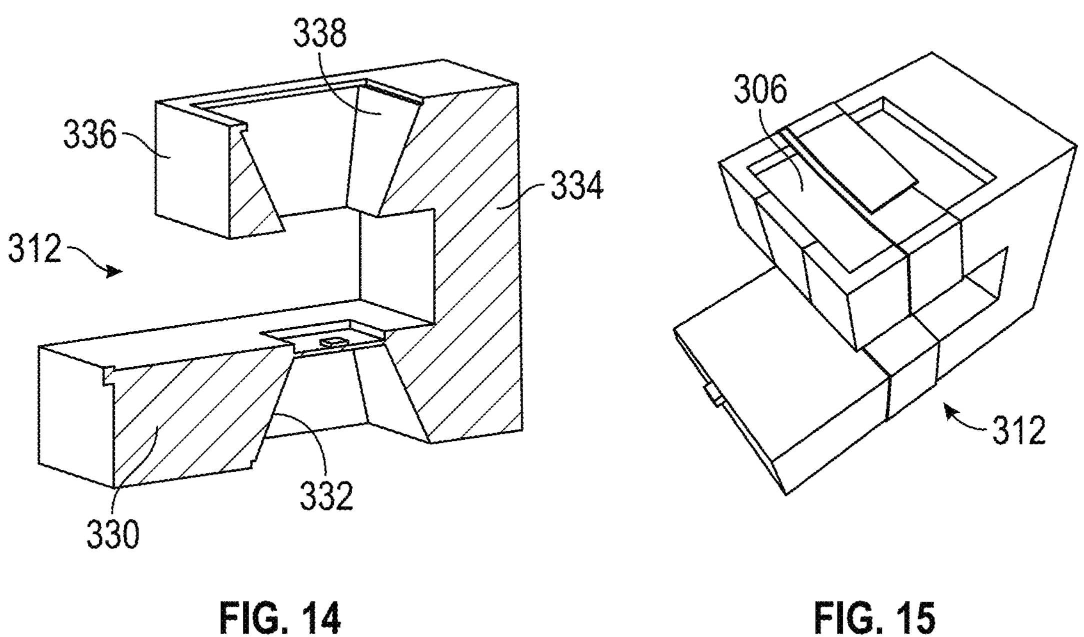
FIG. 14
FIG. 15
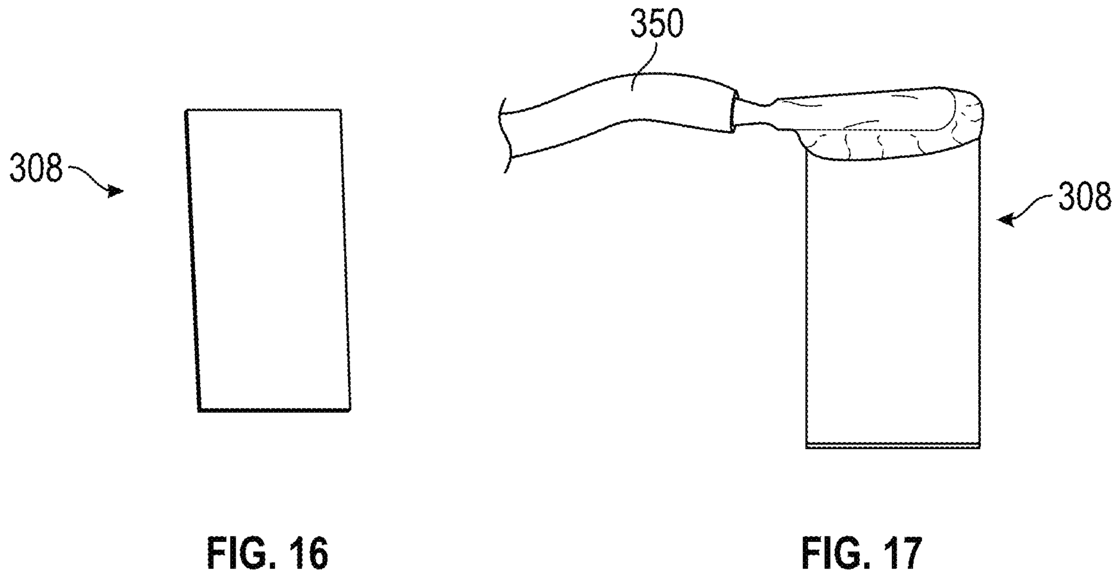
FIG. 16
FIG. 17

404
424
422
428
425

430
420,426

FIXATION DEVICE WITH ELECTROMAGNETIC PUMP

CROSS REFERENCE TO RELATED APPLICATION

This application is a continuation of PCT Application No. PCT/US2023/029437, filed Aug. 3, 2023, which claims the benefit of U.S. Provisional Application No. 63/395,685, filed Aug. 5, 2022, the entire contents of each of which are incorporated by reference herein.

ACKNOWLEDGMENT OF GOVERNMENT SUPPORT

This invention was made with government support under W81XWH-21-1-0179 awarded by the U.S. Army Medical Research and Development Command. The government has certain rights in the invention.

FIELD

The present disclosure concerns devices and methods for generating interstitial fluid flow to promote healing or recovery of bone fracture and wound healing.

BACKGROUND

Mechanical loading or stresses have been known to affect bone remodeling and are used to treat bone diseases and injuries through therapies such as physical activities and whole-body vibrations. However, studies have shown that the magnitude of typical mechanical loading, such as from physical activity, would not be able to cause bone cells to respond. For example, while typical bone strains during locomotion are between 0.04% and 0.3% (and rarely reach 0.1%), many in vitro studies have shown that bone cells need 1-10% of physical deformation to generate a response. The mismatch between the macroscopic (bone) and microscopic (cellular) responses can be explained by the bone structure, which consists of canals that convert small mechanical deformations to fluid flow with much larger drag force and shear stress. This implies that bone cells may not actually be responding to the mechanical strains from the bone, but instead reacting to the resulting amplified fluid flow.

Based on the current understanding of how mechanical loading can improve healing of critical-size bone defects, treatments have emphasized the need for functional loading during bone regeneration. However, recent studies have shown that early functional loading is detrimental to bone healing due to disruption of bone callus formation from the mechanical strain, but that delayed loadings are beneficial. Essentially, these studies suggest there should be a waiting period before employing mechanotransduction effects, e.g., mechanical strain, to accelerate bone healing.

In vitro studies have provided some understanding on the underlying physical phenomenon that bone cells respond to, however, no similar studies have been conducted in vivo. Therefore, many explanations for the mismatch between macro and microscopic effects of mechanical loading rely on models and indirect conclusions from in vitro observations or in silico results. One of the major reasons for the lack of in vivo experiments to verify the micro/macroscopic mismatch described previously is due to the challenge of generating fluid flow without also creating mechanical strain.

Accordingly, a need exists in the art for improved devices and methods capable of generating fluid flow without also creating mechanical strain.

SUMMARY

Described herein are devices and methods that can induce controllable flow of interstitial fluid in vivo at a selected site without mechanically compressing, straining, or pressuring the tissue. The examples described herein can be used for a novel therapy that can treat bone diseases, accelerate healing of bone fractures, and accelerate healing of wounds such as lacerations. The disclosed examples, some of which are based on a specially designed implantable bone fixation assembly, can induce controllable flow of interstitial fluid within a bone fracture site without mechanically compressing, straining, or pressuring the tissue.

Such systems can operate by generating a magnetic field and an electric current at a perpendicular angle to one another, resulting in an out-of-plane electromagnetic (EM) force. The EM force induces the electrically conductive interstitial fluid to flow. The flow rate, direction and frequency can be controlled by altering the magnetic field, the electric current, or both. The examples utilizing a disclosed fluid pump (referred to as a magnetohydrodynamic pump (MHD)) advantageously do not rely on mechanical pressure/movement to achieve the interstitial flow. Therefore, the examples described herein deliver a potential stimulus to bone healing (fluid flow) while avoiding the disruptive factor (mechanical load), without a waiting period. Early fluid flow therapy coupled with later therapy of combined fluid flow and mechanical loading can advantageously improve critical-size defect bone healing. The described examples may further improve treatments for other musculoskeletal injuries such as compartment syndrome or muscle repair in which flow-mediated mechanical stimuli might be beneficial for tissue regeneration.

Current bone fracture therapies based on cell mechanotransduction rely on mechanical loading/stresses such as physical activities and vibration therapies. However, mechanical loading may not be the key driver for bone healing, rather, it may be the resulting fluid flow due to the deformation of bone from the loading. There have also been studies showing that a high level of mechanical loading at the early stage of recovery is detrimental to bone formation. The devices and methods described herein directly provide the healing factor to bone healing (fluid flow) while avoiding the disruptive factor (mechanical load). Additionally, these devices and methods bypass the waiting period needed by the mechanical therapy and can be used to treat patients soon after injury. Such devices and methods therefore provide better outcomes of bone fracture healing. The examples herein not only improve the understanding of bone maintenance and regeneration but also provide better therapies that are based on cell mechanotransduction.

Fluid shear stress (FSS) is an important parameter that regulates various cell functions such as cell proliferation and cell migration. While there are a number of techniques to generate FSS in vitro, many of them require physical deformation or movement of solid objects to generate the fluid shear, preventing the study of FSS in the absence of mechanical force. The devices and methods described herein use a non-mechanical means to generate fluid flow and FSS in various settings including in vivo and in a 2D in vitro setting. In some examples, this is accomplished with a magnetohydrodynamic (MHD) pump, which creates liquid flow by generating a Lorentz force through the interaction between an electric field and an orthogonal magnetic flux. Due to the fluid flow generation without mechanical force, the examples of MHD systems disclosed herein can be implemented to study the role of FSS and electric field on wound healing in vivo.

In some examples, an assembly for promoting interstitial fluid flow can comprise an implant configured to be disposed at a selected site of a subject, the implant comprising spaced apart first and second electrodes. The assembly can further comprise a control unit electrically coupled to the first and second electrodes, the control unit configured to provide power to the first and second electrodes to generate an electric field at the selected site. The assembly can further comprise one or more magnets disposed adjacent to the selected site, the one or more magnets configured to generate a magnetic field in a direction orthogonal to the electric field in order to drive interstitial fluid flow at the selected site.

In some examples, a method of treating a subject in need thereof can comprise disposing the assembly at the selected site and generating the electric field orthogonal to the magnetic field at the selected site for a predetermined duration of time.

In some examples, an assembly for promoting interstitial fluid flow can comprise a bone fixation implant comprising a bone fixation plate configured to be coupled to a bone of a subject at a location of a fracture, first and second electrodes that are spaced apart from one another, and a control unit electrically coupled to the first and second electrodes, where the control unit is configured to actuate the first and second electrodes to generate an electric field at the fracture. The assembly can further comprise one or more magnets disposed adjacent to the fracture, where the one or more magnets are configured to generate a magnetic field in a direction orthogonal to the electric field in order to drive interstitial fluid flow at the fracture.

The foregoing and other objects, features, and advantages will become more apparent from the following detailed description, which proceeds with reference to the accompanying figures.

BRIEF DESCRIPTION OF THE DRAWINGS

FIG. 12 is a perspective view of a MHD system, according to an example.

FIG. 13A illustrates a perspective view of the channel structure of the MHD system of FIG. 12.

FIG. 13B illustrates a top view of the channel structure of the MHD system of FIG. 12, and further shows the channel structure coupled to a petri dish.

FIG. 14 is a cross-sectional perspective view of the support structure of the MHD system of FIG. 12.

FIG. 15 is a top perspective view of the support structure of the MHD system of FIG. 12.

FIG. 16 is a top view of an electrode of the MHD system of FIG. 12.

FIG. 17 is a top view of the electrode of FIG. 16 with a wire connected thereto.

DETAILED DESCRIPTION

General Considerations

Figure 1:
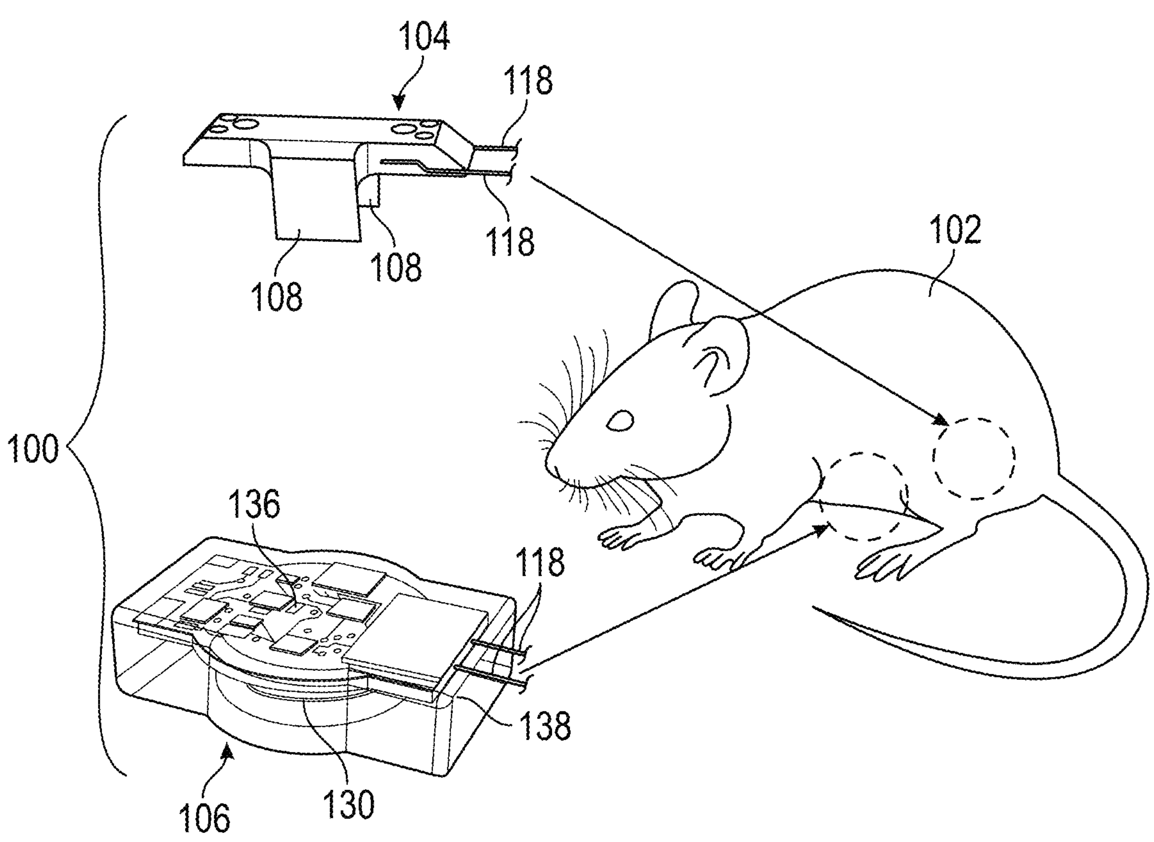
FIG. 1 illustrates a bone fixation assembly, according to an example.

For purposes of this description, certain aspects, advantages, and novel features of the examples of this disclosure are described herein. The disclosed methods, apparatus, and systems should not be construed as being limiting in any way. Instead, the present disclosure is directed toward all novel and nonobvious features and aspects of the various disclosed examples, alone and in various combinations and sub-combinations with one another. The methods, apparatus, and systems are not limited to any specific aspect or feature or combination thereof, nor do the disclosed examples require that any one or more specific advantages be present or problems be solved.

Although the operations of some of the disclosed examples are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

All features described herein are independent of one another and, except where structurally impossible, can be used in combination with any other feature described herein.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

Examples of the Disclosed Technology

The examples described herein are configured to deliver a stimulus to bone or wound healing (fluid flow) while avoiding the disruptive factor (mechanical load), without a substantial waiting period. Early fluid flow therapy coupled with later therapy of combined fluid flow and mechanical loading can improve critical-size bone healing as well as healing for other wounds that can benefit from increased interstitial flow.

Cells have the ability to detect and convert external physical cues into biochemical signals that activate specific cellular responses depending on where they are located in the body. This process, referred to as mechanotransduction, is a crucial cellular response that plays a role in regulating cell functions such as cell proliferation, cell differentiation, and cell migration as well as extracellular matrix composition.

There are various cues that cells respond to, such as mechanical loading, electrotaxis, chemotaxis, and fluid shear stress (FSS). Among these, FSS is an important stimulus for cell migration and proliferation. For example, FSS caused by interstitial fluid flow can lead to the release of nitric oxide and prostaglandins in bone osteoblasts, which promotes cells to differentiate and build more bone matrix. Flow-induced shear stress can regulate smooth muscle cells and fibroblast migration. In addition, the combination of a DC electric field and FSS can further improve directional fibroblast migration. Cell responses can be examined using in vitro simulations of FSS on cultured cells. In vitro models advantageously allow researchers to understand cellular mechanisms such as the response of endothelial cells to laminar flow or the way bone cells respond to the presence of FSS. Understanding these responses can then be used to determine the level of shear stress required to create tissue engineering constructs and develop better medical products and therapies.

Described herein are various assemblies and implants for producing interstitial fluid flow to increase wound or bone healing according to predetermined treatment starting points, durations, and frequencies. These assemblies and implants can be used in humans, large animals, small animals, and in vitro for studying the effects of stimulated fluid flow and feedback on the tissue healing environment during treatment.

Figure 2:
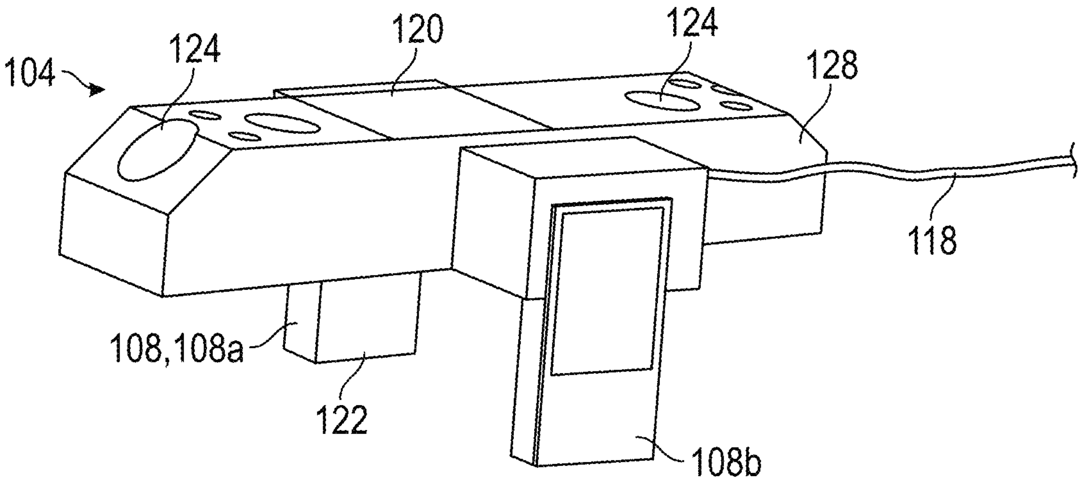
FIG. 2 is a perspective view of the bone fixation plate of the bone fixation assembly of FIG. 1.
Figure 3:
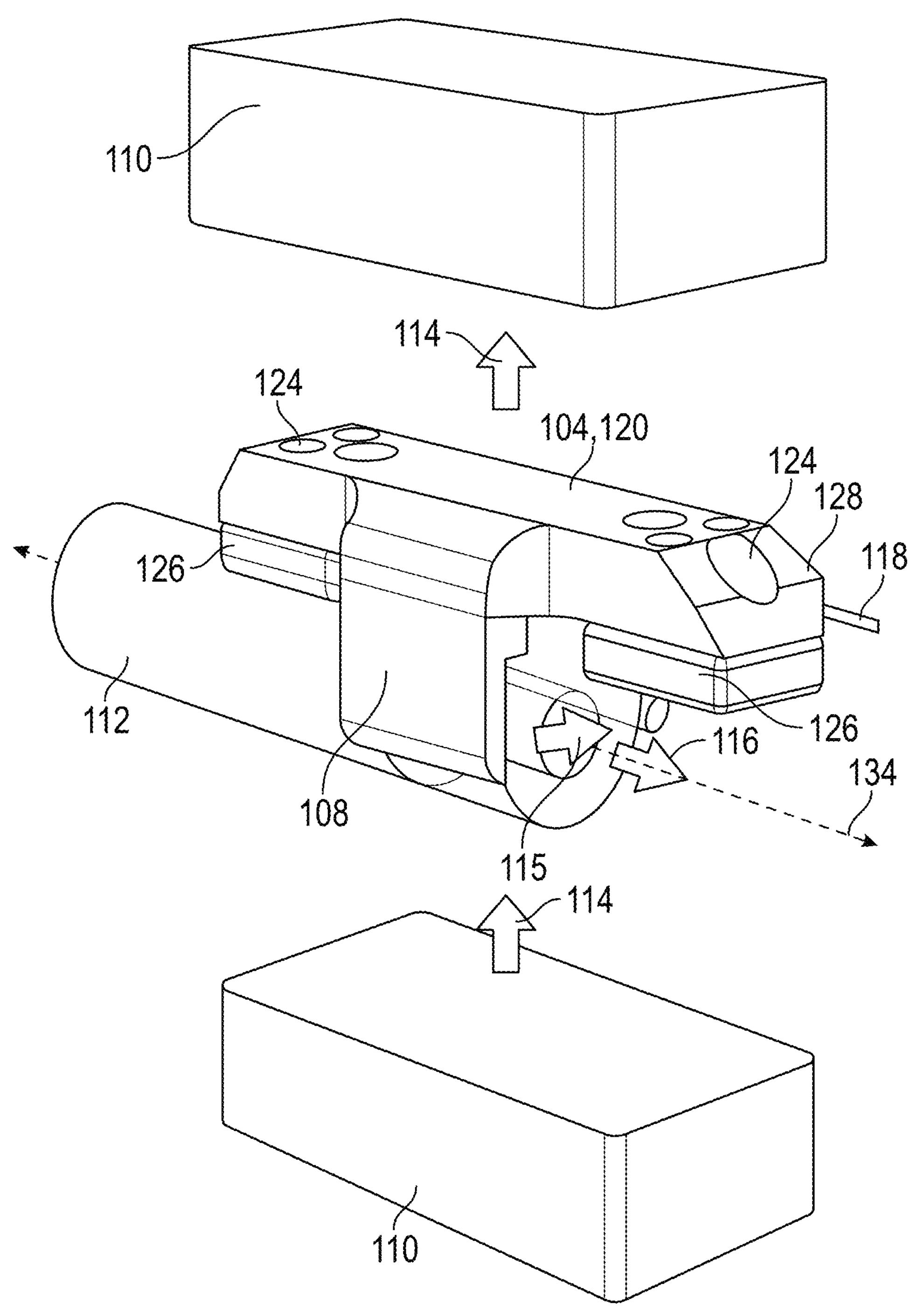
FIG. 3 illustrates the bone fixation plate of the bone fixation assembly of FIG. 1 implanted on a subject's bone and used in connection with external wearable magnets.

FIGS. 1-3 illustrate an exemplary interstitial flow device, also referred to as a fixation device or a bone fixation assembly 100, configured to induce or promote interstitial fluid flow at a bone fracture gap and thereby aid in bone restoration for a critical-size defect in a subject's 102 bone. Referring to FIG. 1, the bone fixation assembly 100 can generally comprise a bone fixation plate 104, a control unit 106 that controls and powers electrodes 108 of the bone fixation plate 104, and one or more magnets 110 (FIG. 3) external to the subject (e.g., worn on a harness). FIGS. 1-4 and Example 1 refer to an instance of the bone fixation assembly 100 being implanted in a non-human subject 102 (e.g., a mouse or rat), however, it should be understood that these examples or other similar examples can also be used in human subjects.

The bone fixation assembly 100 can function using the principles described in Example 2 below, namely, the bone fixation assembly 100 can comprise a magnetohydrodynamic (MHD) pump configured to generate liquid flow due to the application of an electric field across a channel while under a DC magnetic flux that is orthogonal to the electric field. The orthogonally applied electric field and magnetic flux create Lorentz force, expressed in Equation (1), that moves electrically conductive particles (such as interstitial/body fluid) in a direction orthogonal to both the electric field and magnetic flux.

$$F = \sigma E \times B \qquad \text{Equation (1)}$$

where F is the force in N, E is electric field intensity in V/m, B is magnetic flux density in Tesla, $\sigma$ is the conductivity of the material in S $m^{-1}$. Note that F, E and B are vector notations.

The bone fixation assembly 100 uses this force to generate or promote interstitial fluid flow along a defect in a subject's bone 112 (FIG. 3) (e.g., along a longitudinal axis of the bone). As indicated in Equation (1), the magnetic flux density and electric field intensity determine the velocity and direction of the flow, which means that the flow rate can be controlled by varying either the magnetic flux or the electric field across the electrodes (e.g., using the control unit). MHD pumps have several advantages over other types of pumps, including the absence of moving parts, simple flow control, compatibility with a closed-loop flow system, and ease of fabrication and miniaturization. As shown in FIG. 3, in some examples, the magnetic flux flow can be upward in the orientation shown in FIG. 3, as represented by arrows 114, and the interstitial fluid can flow in the direction represented by arrow 116.

Referring to FIG. 1, in the illustrated example, the bone fixation plate 104 and control unit 106 are separate structures coupled by one or more wires 118. Such a configuration advantageously allows the device to be implanted within a smaller subject (e.g., a mouse or rat), by allowing the control unit to be implanted within the abdominal cavity, as shown in FIG. 1. In such examples the wire(s) 118 coupling the bone fixation plate 104 to the control unit 106 can be routed through a small incision in the subject's 102 abdominal wall. However, in other examples (such as the example shown in FIGS. 5-8) the control unit 106 can be mounted on or otherwise coupled directly to the bone fixation plate 104. Although two wires 118 are shown by way of example only in FIG. 1, it should be noted that a different number of wires is possible, such as a single wire that is routed from the control unit 106 to the two electrodes 108.

As shown in FIG. 2, the bone fixation plate 104 can comprise a main body or bone plate 120 configured to be disposed adjacent the subject's bone at the selected implantation site (as shown in FIG. 3), and first and second electrodes 108*a*, 108*b* (which can collectively be referred to as "the electrodes 108) each extending from an opposing side of the main body 120. The electrodes 108 can extend from the main body 120 in the same direction (e.g., down in the orientation shown in FIG. 2), such that a channel 122 is formed between them in which the subject's bone can be disposed (e.g., at the location of a critical-size defect). One or more wires 118 can connect the electrodes 108 to the control unit 106. In some examples, the first electrode 108*a* can be gold anode and the second electrode 108*b* graphite cathode electrodes. In such examples, for example, the gold anode can be created by plating a layer of gold on a copper substrate, and the graphite can be made from fine-grain graphite block. In some examples, both the first and second electrodes 108*a*, 108*b* (anode and cathode) can comprise platinum.

The main body 120 can comprise one or more openings 124 extending through a thickness of the main body 120, which can be used to secure the bone fixation plate 104 to the bone 112 using fasteners (e.g., mechanical means such as bone screws). In other examples, the main body 120 can be secured to the subject's bone 112 using, for example, epoxy, glue, or other biocompatible fastening means. As shown in FIG. 3, in some examples, first and second plates 126 (e.g., stainless steel plates) can be disposed on a first surface of the main body 120 (e.g., the surface adjacent to the subject's bone 112 when the bone fixation assembly 100 is implanted). In such examples, the main body 120 can be secured to the first and second plates 126 via one or more fasteners extending through the openings 124 in the main body, and the first and second plates 126 can be coupled to the subject's bone 112.

The electrically insulated wires 118 that power the electrodes can be guided through tunnels within the main body 120 of the bone fixation plate 104 and exit through its proximal end 128. The electrodes 108 (e.g., gold and graphite) can be secured to two slots at the sides of the main body 120. The entire bone fixation plate 104 can then be sealed with biocompatible adhesive. All joints will be coated with the adhesive to strengthen the structure and ensure compatibility of the implant.

A power supply 130 (FIG. 1) (e.g., a DC power supply such as a battery) can be connected to the electrodes 108 to generate a varying voltage. The electric current flowing through the electrodes 108 can be measured with a multimeter. As shown in FIG. 1, the power supply can be disposed within the control unit 106.

Figures 9, 10:
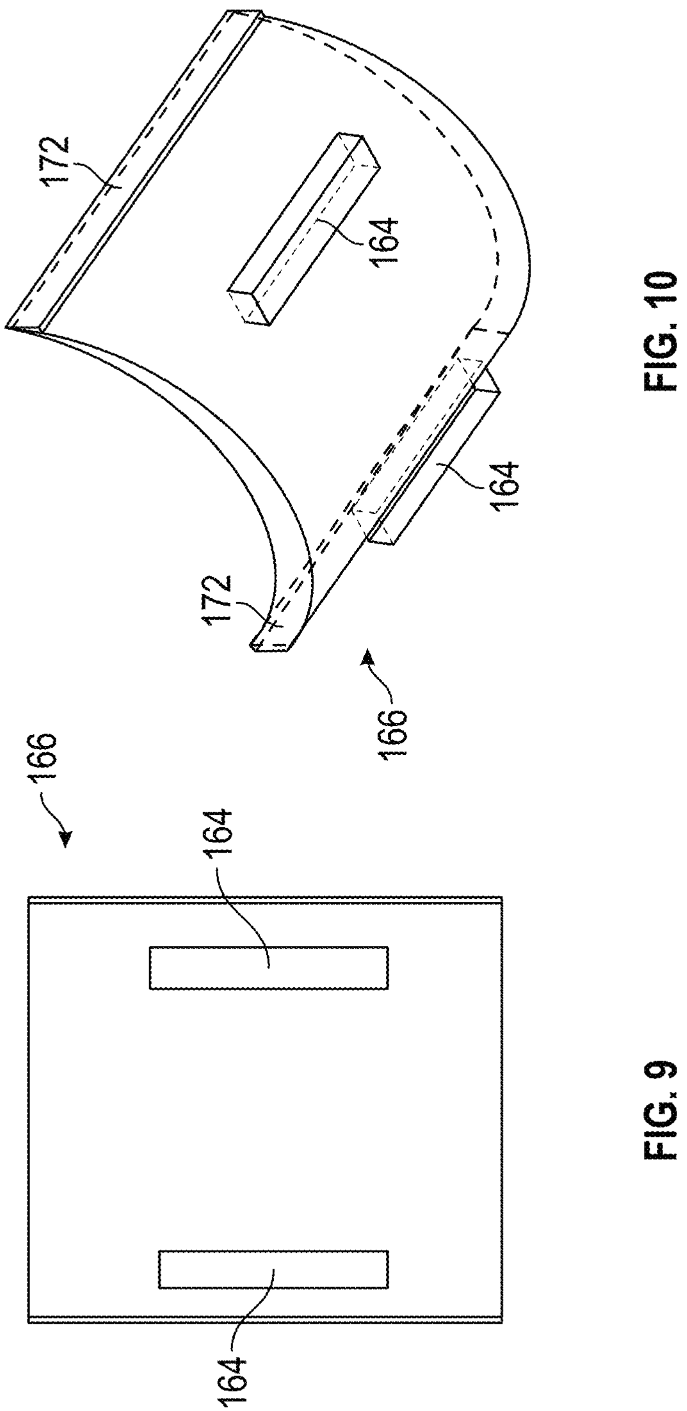
FIGS. 9-10 illustrate various views of a harness for holding one or more magnets of the bone fixation assembly of FIG. 5, according to one example.

Referring to FIG. 3, the bone fixation assembly 100 can further comprise one or more permanent magnets 110 (e.g., first and second magnets). The magnets 110 can be disposed externally to the subject, for example, on a harness/strap/bracelet/wrap/cast worn by the subject. FIGS. 9-10 illustrate an example of a strap or harness 166 comprising the one or more magnets 164 (which in some examples can be replaced by magnets 110). The magnets 110 (and other magnets described herein, such as magnets 164) provide a magnetic field perpendicular to the flow direction of the electric current between the electrodes 108. Such a configuration can create an EM force that induces interstitial fluid flow in parallel to the length of the bone, that is, along a longitudinal axis 134 (FIG. 3) of the bone. In some examples, the magnets 110 can be neodymium permanent magnets.

Figure 4:
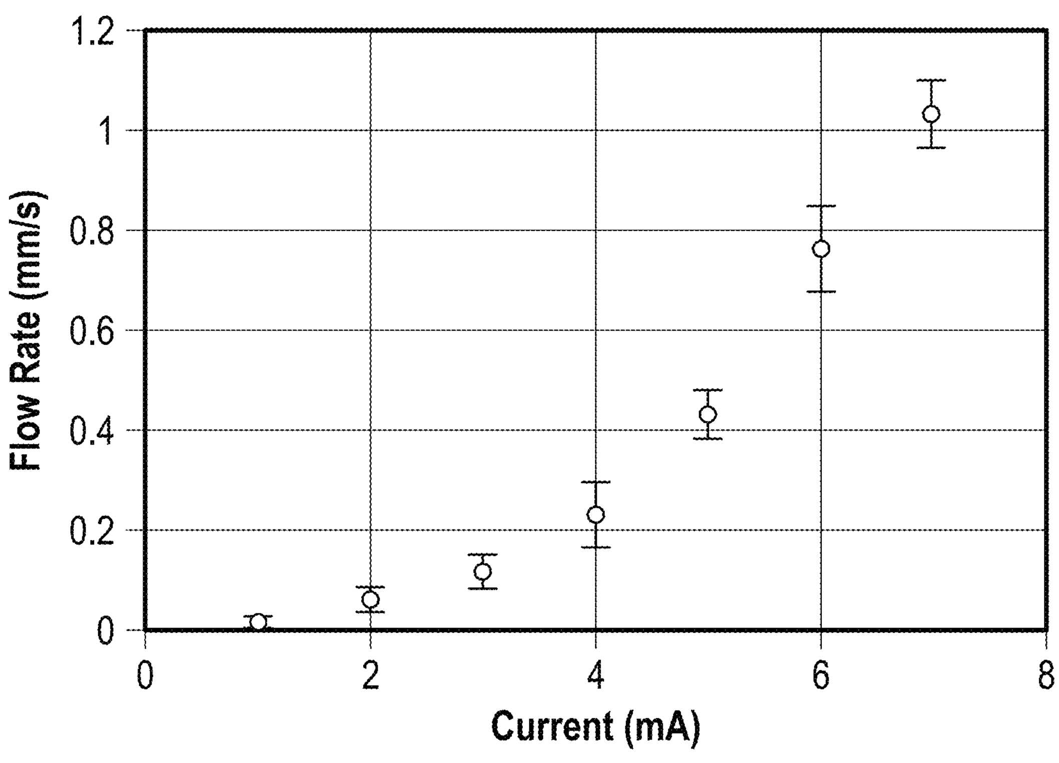
FIG. 4 is a chart illustrating liquid motion as a function of current across electrodes.

FIG. 4 shows a chart of the motion of the interstitial fluid as a function of the current across the electrodes. As shown, a current of 7 mA is sufficient to generate a flow of PBS at 1 mm/s.

In some particular examples, the main body 120 can have dimensions of about 24 mm×about 5 mm×about 3 mm, and the plates 126 can have dimensions of about 6 mm×about 5 mm×about 2 mm. In some examples, the electrodes 108 can have dimensions of about 6 mm×about 4 mm.

In some particular examples, the bone fixation plate 104 can comprise polysulfone (PSU). The higher flexural stiffness of PSU plates (about 250 N/mm as compared to softer polymeric bone plates that typically have a stiffness of about 100 to about 150 N/mm) significantly reduces the effect from mechanical loading when the test subject is walking. This can advantageously allow the bone plate to induce mechanotransduction from only fluid flow.

Referring again to FIG. 1, the control unit 106 can comprise a microcontroller 136, a current supply, and a power supply 130 (e.g., a battery). The microcontroller 136 can comprise one or more CPUs, memory, programmable input/output peripherals, or combinations thereof. The microcontroller 136 can further comprise a wireless communications unit capable of bidirectional communication (e.g., transmitting/receiving). For example, the wireless communications unit can comprise integrated Bluetooth Low-Energy (BLE) bidirectional communication for the user (via a remote control unit) to initiate the flow and control its duration and speed. In some examples, the wireless communications unit can be a BLE113 Bluetooth Smart Module. The control unit 106 can communicate with and be controlled by a remote control unit, such as a smart phone, computer, tablet, remote control, etc. that is remote from the bone fixation assembly 100.

With relays, the microcontroller 136 can turn on the current supply upon user initiation through Bluetooth (e.g., via the remote control device). The current supply can be used to supply a current of up to 1 mA through the electrodes. In some examples, the current supply can be an LT3092 (Analog Devices) adjustable current source controlled using a digital rheostat (Analog Devices, AD5246). The power supply can be a 400 mAh lithium-polymer battery. As shown in FIG. 1, the control unit 106 can be enclosed in a housing 138 (shown transparently in FIG. 1) and sealed with an adhesive cure to form a watertight enclosure. In some examples, the housing 138 can comprise FormLabs Dental LT resin and the adhesive cure can comprise Dymax 1072-m.

In use, when the bone fixation plate 104 is implanted in a subject and secured to the bone 112 (e.g., as depicted in FIG. 3), and the magnets 110 are arranged at a perpendicular orientation from the electrodes 108 (e.g., as shown in FIG. 3), the control unit 106 can be activated (e.g., using a remote control unit) to provide the electrical field. For example, the control unit 106 can activate the electrodes 108 (e.g., by sending current to the electrodes), which can create a current flow and electrical field in the direction that extends between the electrodes, as shown by arrow 115 in FIG. 3. The magnets 110 create the magnetic flux flow in the direction shown by arrows 114 in FIG. 3. can be upward in the orientation shown in FIG. 3, as represented by arrows 114, and the interstitial fluid can flow in the direction represented by arrow 116. The orthogonally applied electric field and magnetic flux create Lorentz force to generate or promote interstitial fluid flow along the fracture (in the direction shown by arrow 116 in FIG. 3), thereby causing FSS.

In another example, the power supply 130 can be a rechargeable battery and a power charging system can be implemented. A wireless charging system can be used to recharge the battery through loosely-coupled induction while the device is implanted. In such examples, the battery charger can be, for example, an MCP73831 battery charger. A receiving coil can be included in the housing 138 for the control unit 106, and a power-charging transmitter can be used to charge the bone fixation assembly 100. In examples where the subject 102 is a non-human animal, the power charging transmitter can be a pad on which the subject can rest during charging.

The bone fixation assembly 100 advantageously allows for remote activation of the bone fixation plate 104 to induce controllable flow of interstitial fluid within a bone fracture site without mechanically compressing, straining, or pressuring the tissue. Furthermore, the described examples of the technology can result in novel bone healing therapies. For example, for severe bone fractures, these examples can deliver a potential stimulus to bone healing (fluid flow) while avoiding the disruptive factor (mechanical load) without a waiting period once treatment begins (such as 2 weeks post implantation of the device), which cannot be accomplished with known technologies. For example, treatment with interstitial fluid flow (using the devices and assemblies described herein) can be started earlier than traditional bone healing therapies (e.g., mechanical loading which may require patients to wait a longer period of time before they can begin loading the injured limb, bone, or the like).

Though the examples herein are primarily described with regard to bone healing/recovery, the principles described herein (namely the use of a magnetohydrodynamic pump to stimulate FSS) can also be used for other types of healing, such as the healing of superficial or non-superficial wounds, such as lacerations. In such examples (see e.g., the example shown in FIG. 11), electrodes 206 can be positioned on a bandage type device 200 for superficial application to a subject. The examples and principles disclosed herein can also improve treatments for other musculoskeletal injuries such as compartment syndrome or muscle repair in which flow-mediated mechanical stimuli may be beneficial for tissue regeneration.

The function and biocompatibility of the bone fixation assembly 100 can be experimentally verified as detailed in Example 1, as described below.

Figure 5:
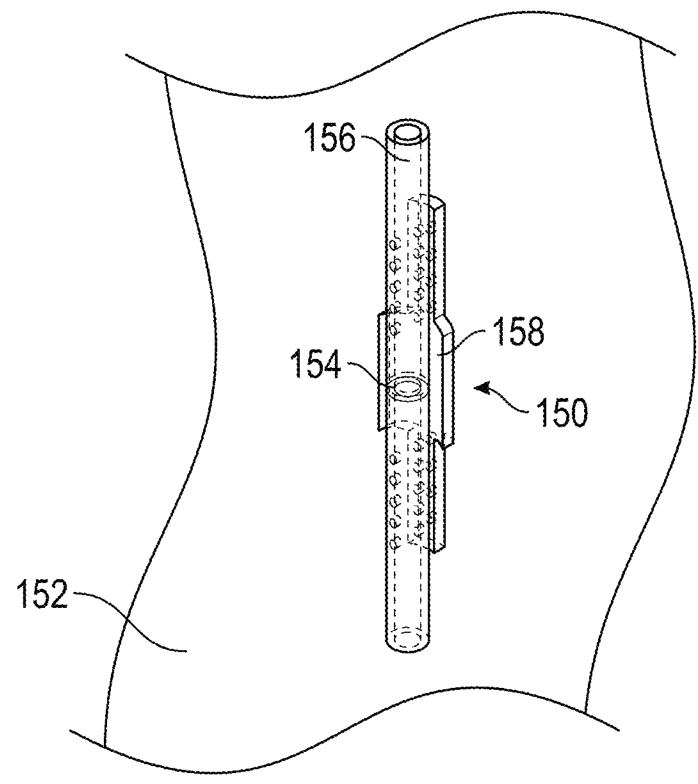
FIG. 5 illustrates a bone fixation assembly, according to an example, implanted on a bone within a subject.

FIGS. 5-8 illustrate another example of a bone fixation assembly 150 configured for implantation in a larger subject, such as a human or a large non-human animal. FIG. 5 shows bone fixation assembly 150 implanted within a human subject 152 with the bone fixation plate 158 disposed over a fracture 154 in the subject's femur 156.

Figure 6:
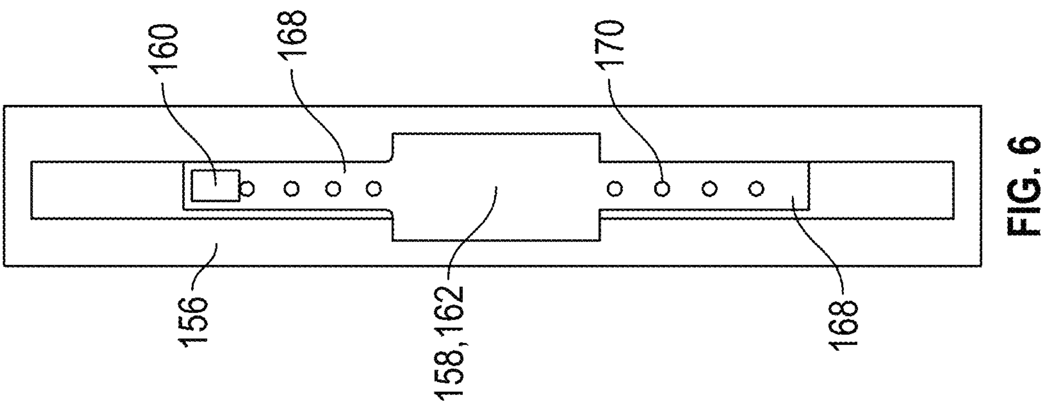

As shown in FIG. 6, bone fixation assembly 150 is similar to bone fixation assembly 100, having a bone fixation plate 158, a control unit 160, one or more electrodes (coupled to the bone fixation plate), and one or more magnets 164 disposed externally to the subject (see FIGS. 9-10, which illustrate a harness 166 configured to hold the magnets 164 adjacent the implantation site).

Figure 8:
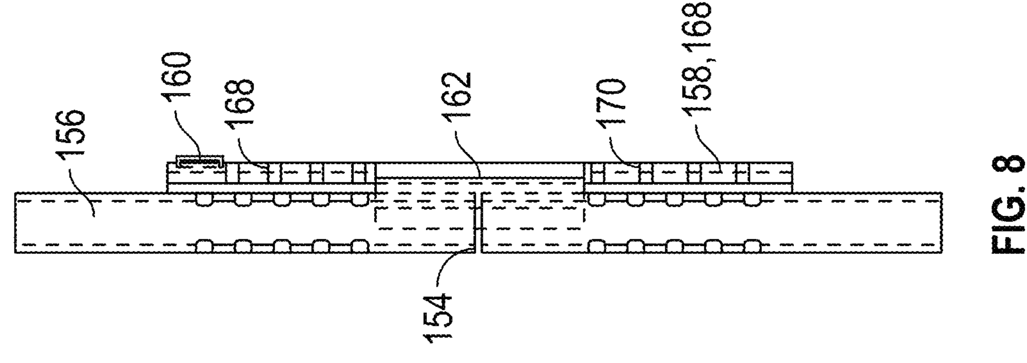
FIGS. 6-8 illustrate various views of the bone fixation assembly of FIG. 5 implanted on a bone.
Figure 7:
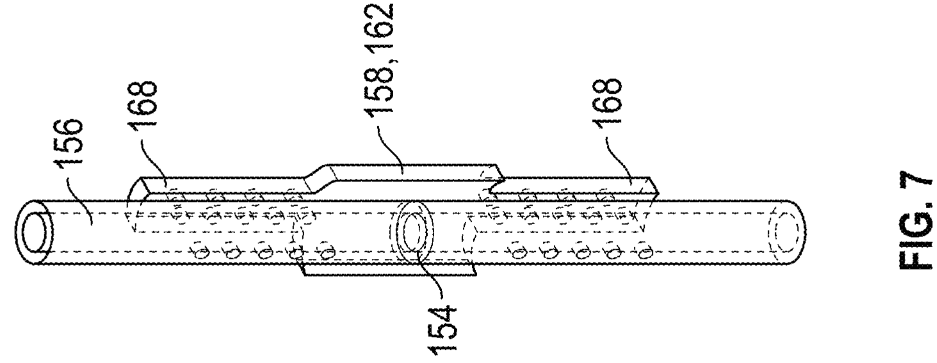

As shown, bone fixation plate 158 has an elongated configuration (e.g., when compared to bone fixation plate 104). This allows the bone fixation plate 158 to span the longer distances required for implantation within a larger subject, such as a human or a large non-human animal. As shown in FIGS. 6-8, the bone fixation plate 158 can comprise a main body 162 and first and second extension members 168 extending from the main body in opposing directions (e.g., up and down in the orientation shown in FIG. 6). As shown in FIG. 7, the bone fixation plate 158 can have a curved shape in cross-section, such that it can correspond to the shape of the outer surface of the subject's bone (e.g., the cortex). The bone fixation plate 158 can comprise one or more apertures or openings 170 extending through a thickness of the bone fixation plate through which one or more fasteners can extend to couple the bone fixation plate 158 to the subject's bone. In the illustrated example, the apertures 170 are disposed on the extension members 168, however in other examples the apertures 170 can be disposed at any location on the bone fixation plate 158, including the main body 162. As shown in FIGS. 6-8, the bone fixation assembly 150 can be implanted such that the main body 162 of the device aligns with the fracture 154 in the subject's bone.

Figures 34A, 34B, 34C, 34D, 34E:
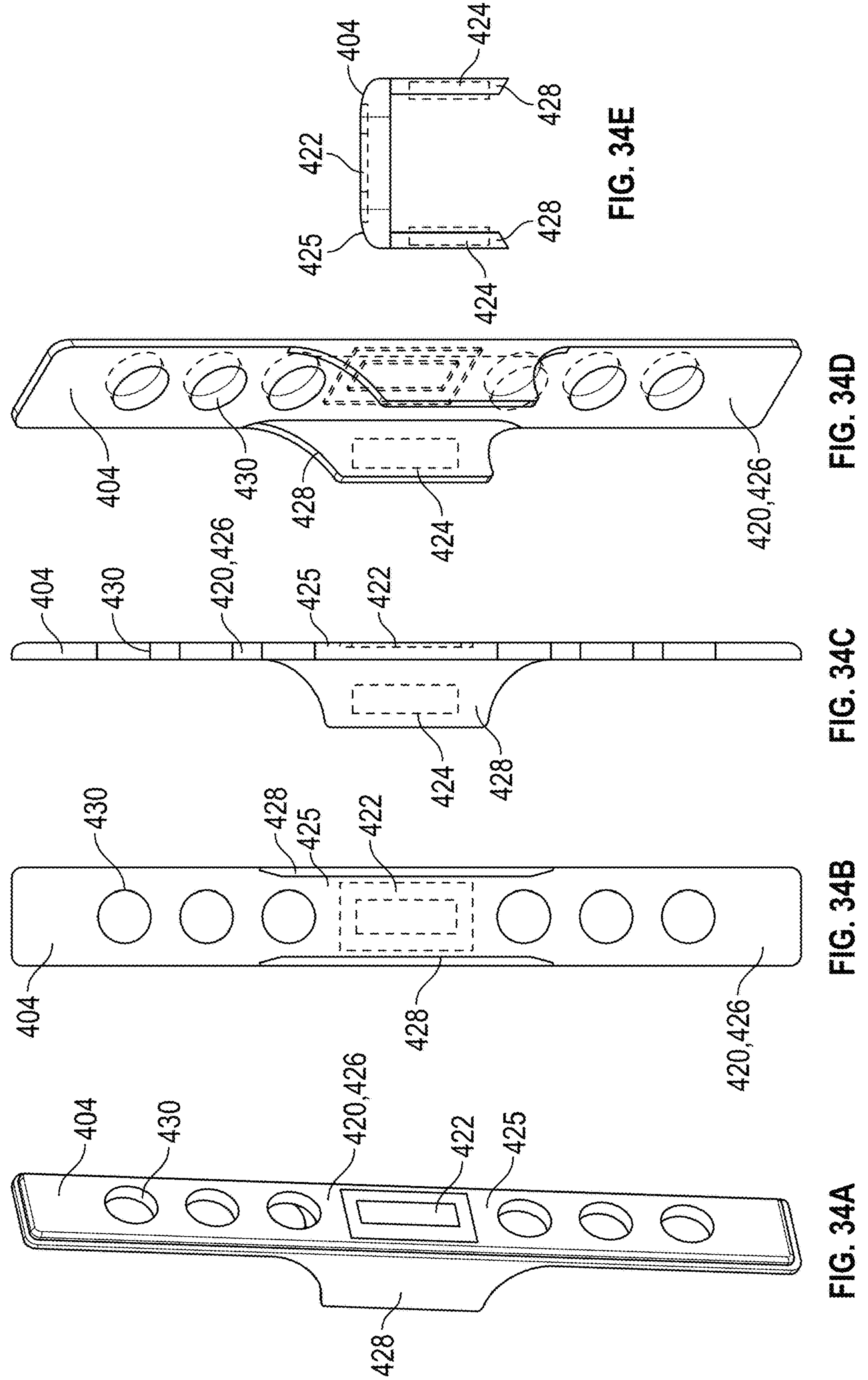
FIG. 34A is a front perspective view of the bone fixation implant of FIG. 31.
FIG. 34B is a rear view of the bone fixation implant of FIG. 31.
FIG. 34C is side perspective view of the bone fixation implant of FIG. 31.
FIG. 34D is rear perspective view of the bone fixation implant of FIG. 31.
FIG. 34E is a top view of the bone fixation implant of FIG. 31.

In the illustrated example, the one or more electrodes (e.g., two electrodes in the described example, such as electrodes 424 shown in FIGS. 34C-34E) are disposed within the main body 162. However, in other examples, the electrodes can be disposed on a first surface of the main body 162 (e.g., adjacent the subject's bone, or coupled to the side portions of the main body 162 similar to the configuration shown for electrodes 108 of bone fixation assembly 100).

The control unit 160 can be disposed on the bone fixation assembly 150, as shown in FIG. 6. In the illustrated example the control unit 160 is disposed on the upper extension member 168, however, in other examples the control unit 160 can be disposed at any location on the bone fixation plate 158 (including on the opposing surface, on the lower extension member, or on the main body 162). Control unit 160 can be similar to control unit 106 described previously. Namely, control unit 160 can comprise a microcontroller, a current supply, and a power source (e.g., a battery). The microcontroller can comprise one or more CPUs, memory, programmable input/output peripherals, or combinations thereof. The microcontroller can further comprise a wireless communications unit capable of bidirectional communication. For example, the wireless communications unit can comprise integrated Bluetooth Low-Energy (BLE) bidirectional communication for the user to initiate the flow and control its duration and speed. In some examples, the wireless communications unit can be a Silicon Labs BLE113 Bluetooth Smart Module. The control unit 160 can communicate with and be controlled by a remote-control unit, such as a smart phone, computer, tablet, remote control, etc. that is remote from the bone fixation assembly 150.

FIGS. 9-10 illustrate an example of a wearable strap/cuff/harness 166 configured to be worn by a subject to position the magnets 164 adjacent the implantation site. The harness 166 can be a flexible strip of material (e.g., fabric) to which the magnets 164 are coupled. The harness 166 can comprise a closure 172 (such as Velcro) configured to allow the harness 166 to be secured around a portion of the subject's body, thus allowing the subject to wear the harness 166 without the subject needing to hold it in place. In other examples, the closure can be, for example, a zipper, a latch, buttons, adhesive, etc. In still other examples, the harness 166 can be configured as a stretchable annular member and the harness can be stretched around the necessary portion of the body to position the harness at the implantation site.

In the illustrated example, the magnets 164 have an elongated bar shape. However, in other examples, the magnets can have any of various shapes (such as square, oblong, circular, hour-glassed shape, or the like). The magnets 164 can be disposed on the harness 166 in a spaced-apart configuration such that when the harness is coupled to the subject the magnets are positioned to provide a magnetic flux orthogonal to the electric field.

The bone fixation assembly 150 can be used in a similar manner as described for bone fixation assembly 100. Namely, the bone fixation plate 158 can be implanted in a subject at a selected location (e.g., adjacent a fracture in the subject's bone), and the harness 166 can be disposed externally on the subject's body at a location corresponding to the implantation site. So positioned, the control unit 160 can be activated (e.g., using a remote-control unit) to provide the electrical field via activation of the electrodes. The orthogonally applied electric field and magnetic flux create Lorentz force to generate or promote interstitial fluid flow along the fracture, thereby causing FSS. Similar to bone fixation assembly 100, bone fixation assembly 150 advantageously allows for remote activation of the device to induce controllable flow of interstitial fluid within a bone fracture site without mechanically compressing, straining, or pressuring the tissue.

Figure 11:
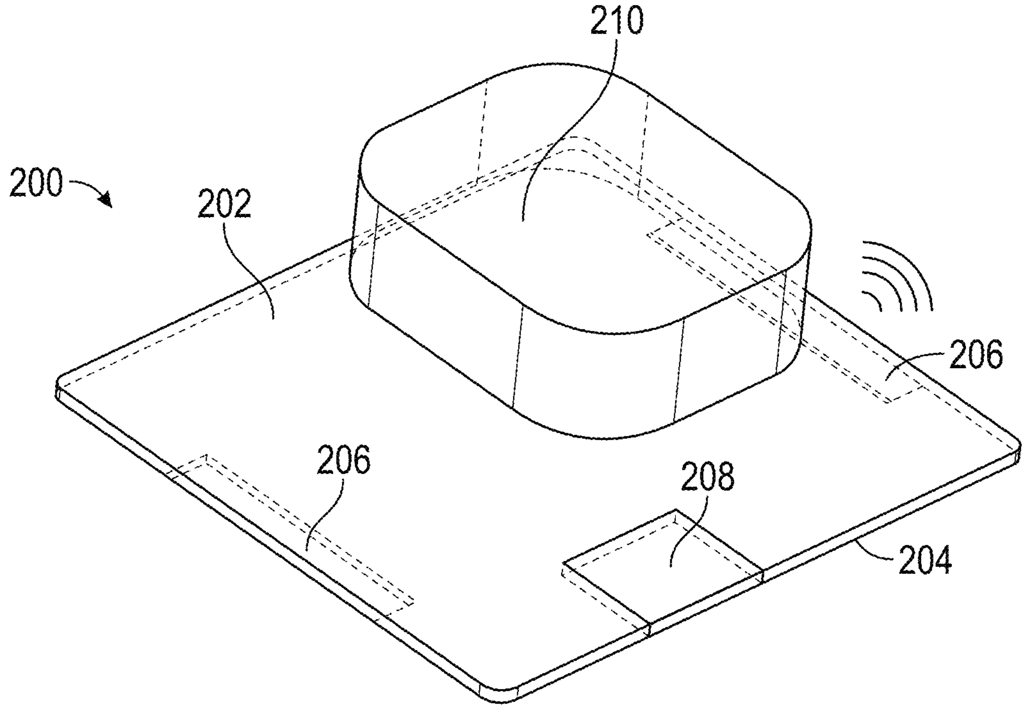
FIG. 11 is a perspective view of a bandage device, according to an example.

FIG. 11 illustrates another example of a device for the generation/promotion of interstitial fluid flow to cause FSS. The bandage device 200 is an externally applied device that does not require implantation within the subject. The bandage device 200 uses a combined application of magnetic flux and an electrical field to cause the flow of interstitial fluid thus promoting FSS at a desired site, such as a wound (e.g., a laceration, surface wound, shallow tissue injury etc.).

The bandage device 200 can comprise a main body 202 comprising an adhesive portion 204, one or more electrodes 206, a control unit 208, and one or more magnets 210. As shown in FIG. 11, the one or more magnets 210 (e.g., one magnet in the illustrated example) can be disposed on the outer surface of the main body 202. In other examples, all or part of the magnet 210 can be disposed within the main body 202.

The main body 202 can be a flexible patch or fabric strip comprising the adhesive portion 204. The adhesive portion 204 can be configured to adhere the bandage device 200 to a subject's skin at a selected location (e.g., adjacent a wound). In some examples, the adhesive portion 204 can comprise a protective cover that can be removed prior to adhering the bandage device 200 to the subject's skin.

The electrodes 206 can be similar to electrodes 108 described previously and can be disposed on or within the main body 202. In some examples, the electrodes 206 can be coupled to the main body 202 using, for example, an adhesive or epoxy, or using other methods of coupling such as sewing the electrodes to the material of the main body 202.

The control unit 208 can be similar to control unit 106 and 160 described previously, and can be disposed on or within the main body 202. Namely, control unit 208 can comprise a microcontroller, a current supply, and a power source (e.g., a battery). The microcontroller can comprise one or more CPUs, memory, programmable input/output peripherals, or combinations thereof. In some examples, the control unit 208 can further comprise a display or alternate input device such that it can be operated directly by the subject, a healthcare provider, or both. In some examples, the micro-controller can further comprise a wireless communications unit capable of bidirectional communication. For example, the wireless communications unit can comprise integrated Bluetooth Low-Energy (BLE) bidirectional communication for the user to initiate the flow and control its duration and speed. In some examples, the wireless communications unit can be a Silicon Labs BLE113 Bluetooth Smart Module. The control unit 208 can communicate with and be controlled by a remote-control unit, such as a smart phone, computer, tablet, remote control, etc. that is remote from the bandage device 200.

The bandage device 200 can be used in the following exemplary manner. The bandage device 200 can be adhered to the subject's skin at a selected location (e.g., over a wound). So adhered, the control unit 208 can be activated (e.g., directly or using a remote-control unit) to provide the electrical field (e.g., via activation of the electrodes 206). The orthogonally applied electric field and the magnetic flux from the magnet 210 create Lorentz force to generate or promote interstitial fluid flow to the wound, thereby causing FSS.

Figure 31:
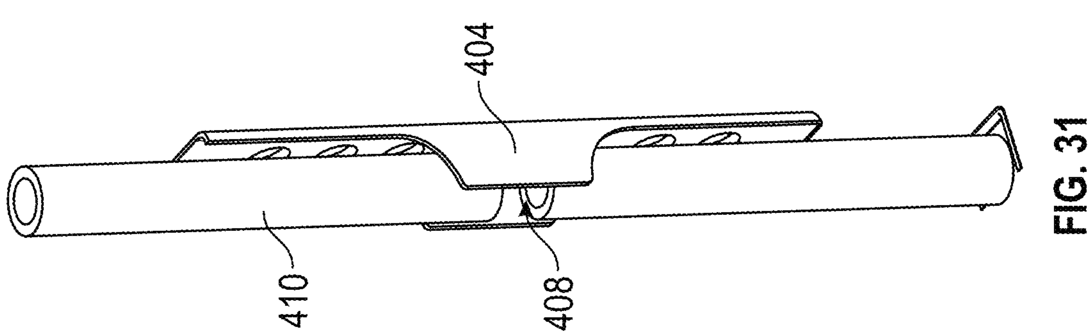
FIG. 31 shows a bone fixation implant of the assembly of FIG. 30 fixed to a bone of the human, at the fracture.
Figure 30:
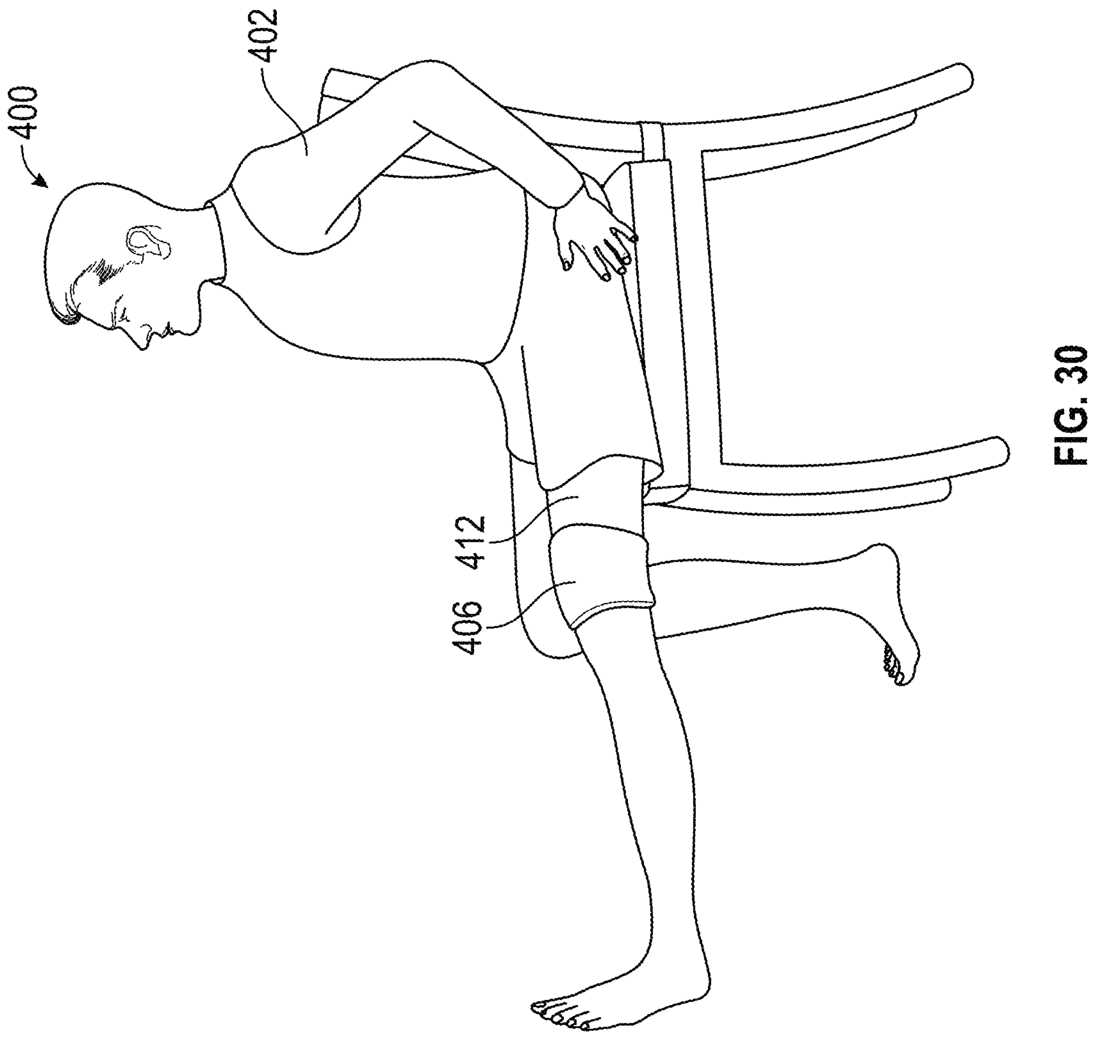
FIG. 30 illustrates an assembly for promoting interstitial fluid flow in a human, the assembly comprising a wearable harness including one or more magnets that is disposed around a leg of the human, around a region of a fracture where a bone fixation implant of the assembly is fixed thereto.
Figure 32:
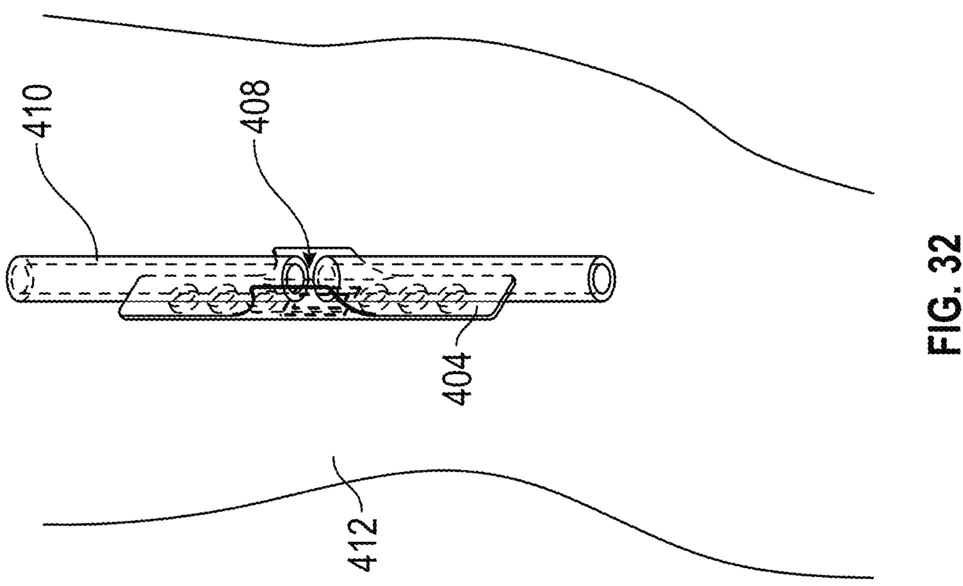
FIG. 32 shows the location of the bone fixation implant of FIG. 31 in the leg of the human.

FIGS. 30-40 illustrate an example of an assembly 400 (a bone fixation assembly, for example) for promoting interstitial fluid flow in a human 402 or a large non-human animal (as depicted in FIG. 30). The assembly 400 comprises a bone fixation implant 404 and a wearable strap/cuff/harness 406 which includes one or more magnets. FIG. 31 shows the bone fixation implant 404 disposed over a fracture 408 in the femur 410 of the human 402. FIG. 32 shows the arrangement of the fractured femur 410 with the bone fixation implant 404 fixed thereto in the leg 412 of the human 402, and FIG. 30 shows the harness 406 disposed over or around the leg 412 of the human 402, around the region of the fracture 408 with the bone fixation implant 404 fixed thereto.

Figure 33:
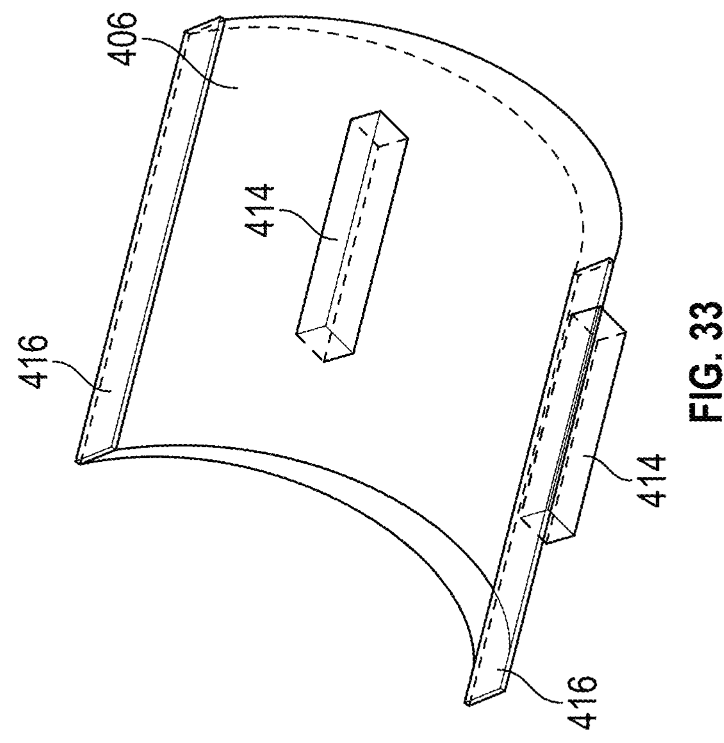
FIG. 33 is a perspective view of an exemplary wearable harness with two spaced apart magnets incorporated therein.

In some examples, such as the example shown in FIG. 33, the harness 406 can be a flexible strip of material (e.g., fabric) to which magnets 414 are coupled. The harness 406 can comprise a closure 416 (such as Velcro) configured to allow the harness 406 to be secured around a portion of the subject's body (for example, the leg 412, as shown in FIG. 30), thus allowing the subject to wear the harness 406 without the subject needing to hold it in place. In other examples, the closure can be, for example, a zipper, a latch, buttons, adhesive, etc. In still other examples, the harness 406 can be configured as a stretchable annular member and the harness can be stretched around the necessary portion of the body to position the harness at the implantation site.

In the illustrated example of FIG. 33, the magnets 414 have an elongated bar shape. However, in other examples, the magnets can have any of various shapes (such as square, oblong, circular, hour-glassed shape, or the like). The magnets 414 can be disposed on the harness 406 in a spaced-apart configuration such that when the harness is coupled to the subject the magnets are positioned to provide a magnetic field/flux orthogonal to the electric field.

In some examples, as shown in FIG. 33, the magnets 414 can be incorporated into the harness 406, such as being embedded within the material of the harness 406.

In some examples, the magnets 414 can be attached to the material of the harness 406, such as being sewn or adhered thereto. For example, in some instances the harness 166 shown in FIGS. 9 and 10 can replace the harness 406 in the assembly 400.

Figures 35A, 35B:
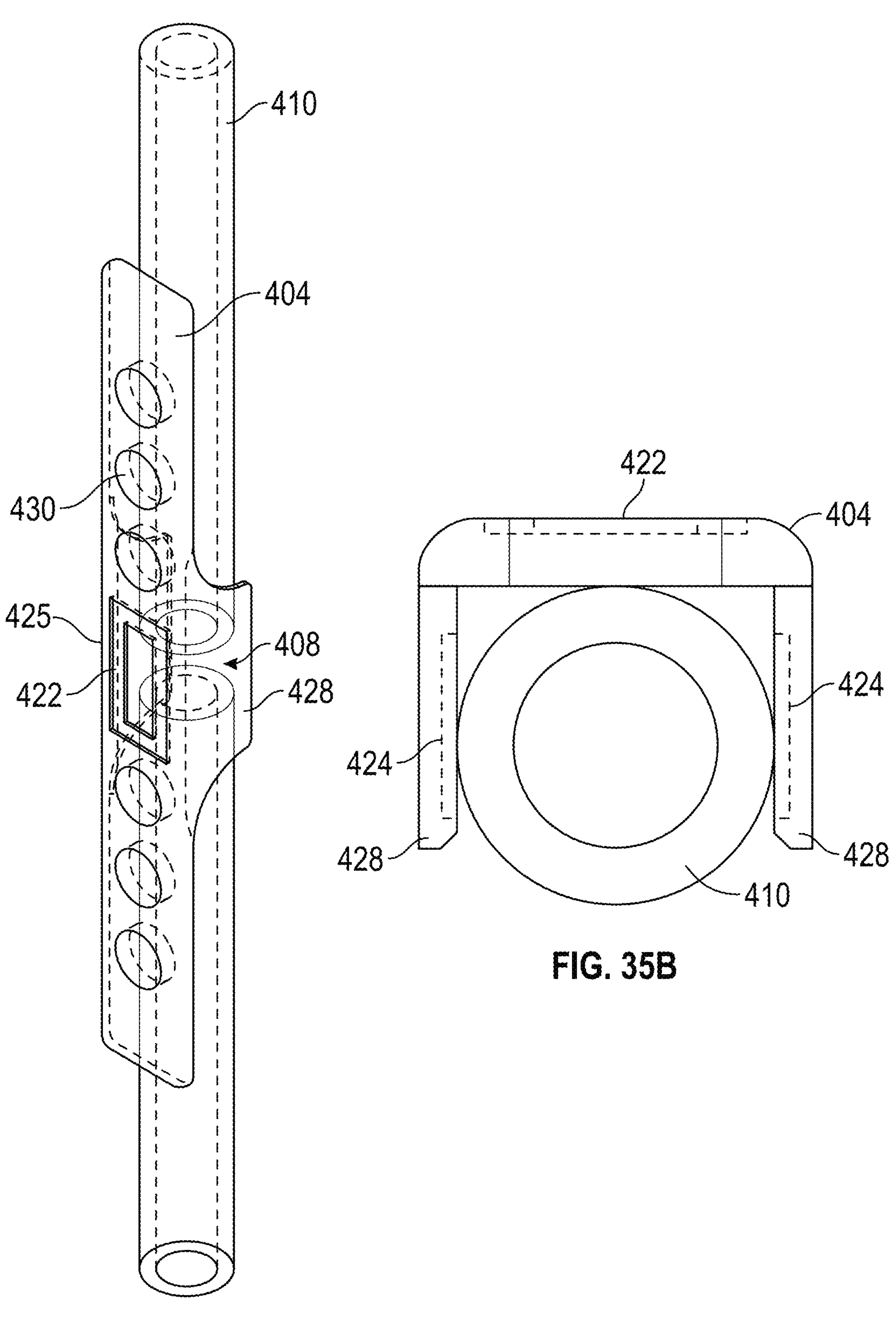
FIG. 35A is a perspective view of the bone fixation implant of FIG. 31 fixed to a bone containing a fracture.
FIG. 35B is a top view of the bone fixation implant of FIG. 31 fixed to a bone containing the fracture.

FIGS. 34A-34E show different views of the bone fixation implant 404 alone, and FIGS. 35A and 35B shows perspective and top views, respectively, of the bone fixation implant 404 coupled to the femur 410 and disposed over the fracture 408. As shown in FIGS. 34A-34E, the bone fixation implant 404 can be similar to the bone fixation assembly 150 described above with reference to FIGS. 5-8 and the bone fixation assembly 100 described above with reference to FIGS. 1-2. For example, the bone fixation implant 404 can include a bone fixation plate 420, a control unit 422, and one or more electrodes 424 (coupled to the bone fixation plate 420). The bone fixation implant 404 can be part of the bone fixation assembly 400 that further includes one or more magnets disposed externally to the subject (for example, magnets 414 of harness 406). In some examples, the bone fixation plate 420 can include the control unit 422 and the one or more electrodes 424 embedded therein or coupled thereto.

As shown, the bone fixation plate 420 has an elongated configuration (e.g., when compared to bone fixation plate 104). This allows the bone fixation plate 420 to span the longer distances required for implantation within a larger subject, such as human 402 or a large non-human animal. In some examples, a length of the bone fixation plate 420 can be customized for one or more of the target bone (e.g., femur vs. humorous vs. clavicle) and a size of the subject (e.g., a child vs. an adult).

As shown in FIGS. 34A-34E, the bone fixation plate 420 can comprise an elongated main body 426 and first and second extension members 428 extending in a same direction from opposite sides of the main body 426. In this way, the first and second extension members 428 can be spaced apart from one another, by an amount that is equal to a width of the main body 426.

In some examples, each of the first and second extension members 428 can comprise an electrode 424 embedded therein or coupled thereto (as indicated by the dashed boxes in FIGS. 34C-34E). In this way, each electrode 424 can be disposed on or in a respective first and second extension member 428. In some examples, the electrodes 424 can be disposed on inner surfaces (the surfaces that face one another and the bone) of the respective first and second extension members 428. In this way, the bone fixation implant 404 can comprise two electrodes 424 spaced apart from one another such that they are disposed on opposite sides of a bone (e.g., the femur 410) when implanted in a subject, as shown in FIGS. 35A and 35B.

In some examples, as shown in FIGS. 34A-34E, the main body 426 can be relatively planar (or flat). In such examples, when the main body 426 is positioned against a surface of the bone, on a first side of the bone (e.g., femur 410), the first and second extension members 428 extend across opposing second and third sides of the bone (as shown in FIG. 35A and FIG. 35B). In this way, the electrodes 424 are disposed on opposite sides of the fracture 408 in the femur 410 (as shown in FIG. 35B).

However, in some examples, the main body 426, the first and second extension members 428, or all of the above, can be curved (such as having a curved cross-section) in order to correspond to the shape of the bone.

The bone fixation plate 420 can comprise one or more openings or apertures 430 extending through a thickness of the bone fixation plate 420, through which one or more fasteners can extend to couple the bone fixation plate 420 to the subject's bone (e.g., femur 410). In the illustrated example, the apertures 430 are spaced apart along the main body 426, on opposite sides of a central portion 425 of the main body 426 (where the control unit 422 is disposed, as explained further below).

The first and second extension members 428 can extend outward from the central portion 425 of the main body 426. As shown in FIG. 35A, the bone fixation implant 404 can be implanted such that the central portion 425 of the main body 426 of the bone fixation plate 420 aligns with the fracture 408 in the subject's bone (e.g., femur 410).

The control unit 422 can be disposed on the bone fixation plate 420, as shown in FIGS. 34A-34E. In the illustrated example the control unit 422 is disposed on the central portion 425 of the main body 426. However, in other examples the control unit 422 can be disposed at any location on the bone fixation plate 420. In some examples, the control unit 422 can be embedded in or attached to an outwardly facing surface of the main body 426 (FIG. 34A) which is opposite an inwardly facing surface of the main body 426 (which is shown in FIGS. 34A and 34D).

The control unit 422 can be similar to the control unit 106, control unit 160, or both, as described previously. Namely, the control unit 422 can comprise a microcontroller, a current supply, and a power source (e.g., a battery). In some examples, the control unit 422 can include an integrated circuit board comprising one or more components which can be electrically connected to the electrodes 424 (e.g., via wires that extend between the control unit 422 and the electrodes 424, as represented by the lines extending between the electrodes 424 and microcontroller 438 in FIGS. 36A and 36B). Example configurations for the control unit 422, within the bone fixation implant 404, are shown in FIGS. 36A and 36B.

Figure 36A:
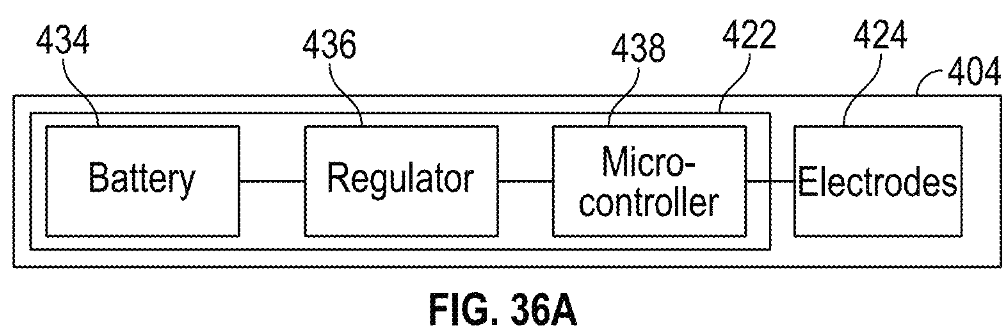
FIG. 36A is a system diagram of an exemplary control system for the bone fixation assembly of FIGS. 30-32, where a power supply of the system is internal to the control unit.
Figure 36B:
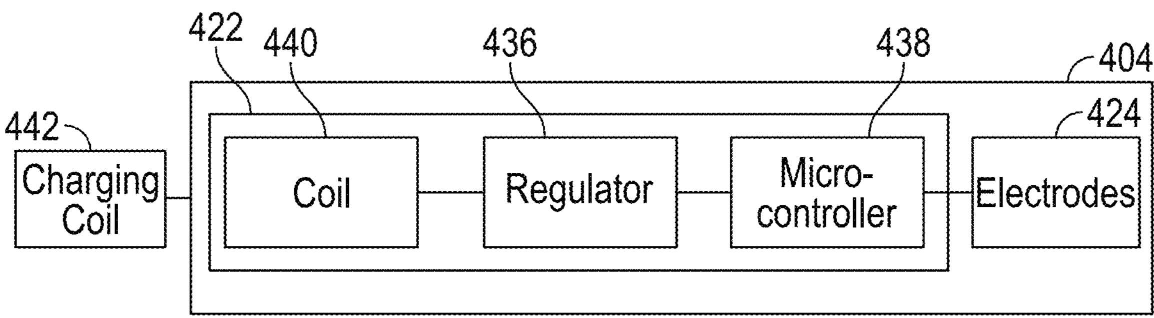
FIG. 36B is a system diagram of an exemplary control system for the bone fixation assembly of FIGS. 30-32, where a portion of the power supply of the system is external to the control unit.

In some examples, as shown in FIG. 36A, the control unit 422 can include an internal battery 434 (or power source or power supply), a regulator 436, and a microcontroller 438. As explained above, the microcontroller can comprise one or more CPUs, memory, programmable input/output peripherals, or combinations thereof. The microcontroller can further comprise a wireless communications unit capable of bidirectional communication. For example, the wireless communications unit can comprise integrated Bluetooth Low-Energy (BLE) bidirectional communication for the user to initiate the flow and control its duration and speed. In some examples, the wireless communications unit can be a Silicon Labs BLE113 Bluetooth Smart Module. The control unit 422 can communicate with and be controlled by a remote-control unit, such as a smart phone, computer, tablet, remote control, etc. that is remote from the bone fixation implant 404.

The regulator 436 can be electrically coupled with the battery 434 and the microcontroller 438 such that it is configured to deliver the appropriate power needed to the various components of the control unit 422. The electrodes 424 can be electrically connected to the control unit 422 within the bone fixation implant 404 (e.g., by wires). As discussed herein, the control unit 422 can be activated (e.g., using a remote-control unit) to provide current to the electrodes 424, and thus create the electrical field.

In some examples, the internal battery 434 can be a lithium-ion battery that is included in the bone fixation implant 404, along with the integrated circuit board (which may include the microcontroller 438 and regulator 436, for example) and electrodes 424 (as shown in FIG. 36A).

In some examples, as shown in FIG. 36B, instead of the internal battery, the control unit 422 can include an internal coil 440 that may be incorporated with the rest of the integrated circuit of the control unit 422. The system or assembly can further include an external charging coil 442 that is not implanted (and may disposed outside of the subject, such as outside of human 402 in FIG. 30). The charging coil 442 can be configured to power up the coil 440 of the control unit 422 as needed (for example, by bringing the charging coil 442 into relatively close proximity of the bone fixation implant 404 (such as adjacent to the harness 406 shown in FIG. 30).

The bone fixation assembly 400 can be used in a similar manner as described herein for bone fixation assembly 100 and 150. Namely, the bone fixation implant 404 can be implanted in a subject (e.g., human 402, as shown in FIG. 30) at a selected location (e.g., adjacent the fracture 408, as shown in FIGS. 31 and 32), and the harness 406 can be disposed externally on the subject's body (e.g., leg 412) at a location corresponding to the implantation site (as shown in FIG. 30). In some examples, the bone fixation implant 404 can be implanted on day one (the day the injury occurs, or as soon following the injury as possible when surgery to stabilize the fracture is possible).

Following implantation, the control unit 422 can be activated (e.g., using a remote-control unit) to provide the electrical field via activation of the electrodes 424. The magnets within the harness 406 apply the magnetic field (or flux) orthogonal to the electrical field (e.g., due to the magnets within the harness 406 being arranged perpendicular to the electrodes 424). The orthogonally applied electric field and magnetic field create Lorentz force to generate or promote interstitial fluid flow along the fracture 408, thereby causing FSS. Similar to the bone fixation assemblies 100 and 150, the bone fixation assembly 400 advantageously allows for remote activation of the bone fixation implant 404 to induce controllable flow of interstitial fluid within a bone fracture site without mechanically compressing, straining, or pressuring the tissue.

In some examples, the control unit 422 can be activated to create the electrical field using the electrodes 424 for the first time at approximately two weeks post implantation of the bone fixation implant 404. This can be referred to as the treatment starting timepoint or treatment initiation time. In some examples, the treatment starting timepoint can be in a range of 14-21 days post-surgery (when the bone fixation implant 404 is implanted, which may be the same or slightly after the day of injury). For example, since in many long bone fracture surgeries, the injury (e.g., bone break) is cleaned and stabilized during surgery, the healing process may properly begin at the time of surgery and implantation of the bone fixation implant.

In some examples, the frequency of treatment (the frequency for activating the control unit 422 to create the electric field) can be 2-3 times per week, at least two times per week, at least three times per week, or 2-4 times per week. In some examples, the duration of each treatment (each application of the electric field and magnetic field) can be 20 minutes (e.g., 20 minutes per treatment day), or in a range of 15-25 minutes, or 15-60 minutes. In some examples, a treatment plan, which may include the treatment starting timepoint, frequency of treatments, and duration of treatments, can vary based on one or more of the subject (e.g., human, large animal, male, female, weight, or the like), and the type of injury (e.g., severity of bone fracture, size of the fracture, or whether it is a tissue injury other than a bone fracture).

In some examples, the bone fixation assembly 400 (or any of the other bone fixation assemblies described herein, such as bone fixation assemblies 100 and 150) can additionally include a feedback system for providing feedback on the status of the healing bone or tissue. For example, an impedance sensor can be integrated within the bone fixation implant 404 to provide feedback on the status of the healing bone or tissue (thus allowing the control unit 422 to adjust the electrical current as needed). In some examples, the impedance sensor can share the same electrodes 424 that are responsible for generating the electrical field.

Different tissues in the body have different impedance responses. As bone, or other tissue, regenerates, the impedance measured across the electrodes 424 will change as well. This feedback can be communicated wirelessly by the control unit 422 (to a wireless receiver, which may be part of an external CPU, for example) and gives accurate information on the healing environment.

Figure 37:
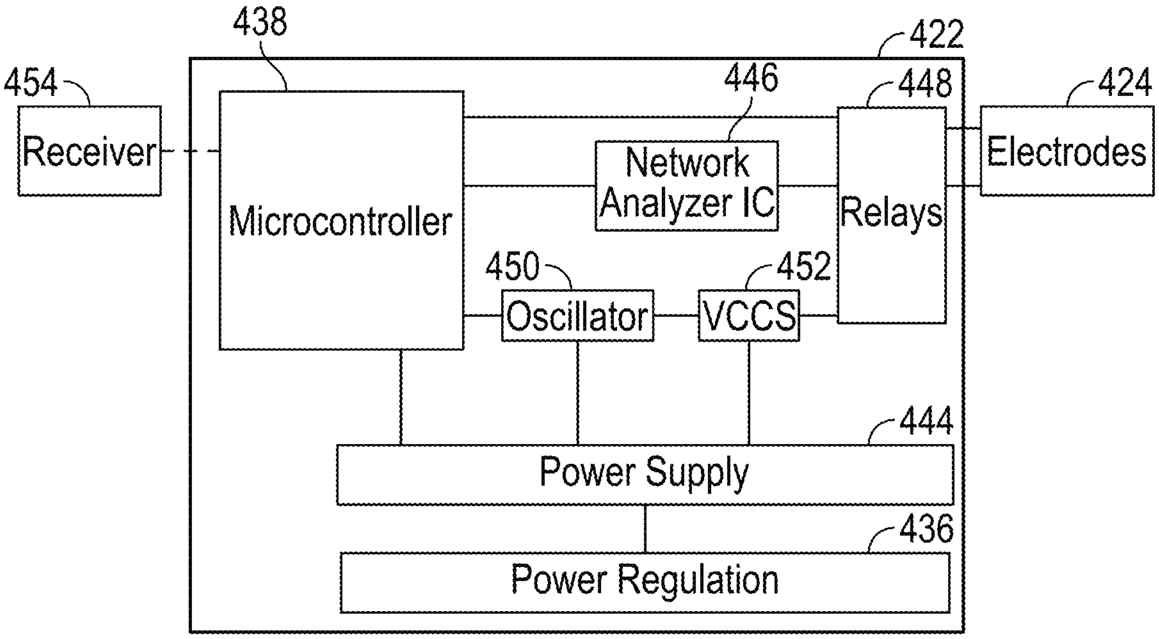
FIG. 37 is a system diagram of an exemplary control system for the bone fixation assembly of FIGS. 30-32, where the system is configured with sensing and stimulating modes using the electrodes of the bone fixation implant.

For example, as shown in FIG. 37, the control unit 422 can include the microcontroller 438, a power supply 444 (which may be the internal battery 434 of FIG. 36A or the internal coil 440 and external charging coil 442 of FIG. 36B), and the power regulator 436. The control unit 422 can further include a network analyzer 446 which is configured to measure the impedance of tissue (or bone) between the two electrodes 424. The control unit 422 can also include relays 448 which switch between sensing and stimulating modes of the electrodes 424. For example, in the sensing mode the signal from the electrodes 424 can provide feedback as to the status of the healing tissue (e.g., the amount of healing) and in the stimulating mode, the electrodes 424 can supply the electric field for generating the interstitial fluid flow. The control unit 422 can also include an oscillator 450 and Voltage controlled current source, or VCCS 452, which are configured to convert the DC signal to a periodic AC signal.

In some examples, the impedance sensing system can also include a receiver 454 (e.g., a wireless receiver), which may be included in a CPU, for example. The receiver 454 can be wirelessly connected to the control unit 422 such that impedance measurements obtained from the electrodes 424 can be processed and utilized by a user. As such, in response to the received impedance measurements, a user can adjust the stimulation settings of the bone fixation implant 404, such as adjusting one or more of the magnitude of the applied electric field (for example, by increasing or decreasing the voltage applied by the control unit 422), the frequency of treatment, and the duration of treatment. The feedback of impedance measurements can also be utilized by a physician or other medical professional to determine the status (amount, progress, or the like) of the healing tissue, and determine whether the patient can resume normal activity or function.

The various bone fixation assemblies described herein (such as bone fixation assemblies 100, 150, and 400) can be implemented in a variety of ways. In some examples, the bone fixation assemblies or devices described herein can be used to investigate fluid flow effects in vivo. For example, data obtained from in vivo studies can be used to determine when treatment with FSS using the bone fixation assemblies described herein should begin after injury and surgery (e.g., two days, one week, two weeks post-injury or post-surgery, or the like), the optimal magnitude and profile of FSS (e.g., pulsing, continuous, or bi-directional flow), the number of treatments per day/week, and the duration per treatment for bone regeneration. In some examples, direct in vivo data on the physiology of bone regeneration can be obtained during in vivo studies, which may allow researchers to study what the optimal or pathological FSS is, which can them be used in developing other therapeutics such as bone tissue constructs.

In some examples, the bone fixation assemblies or devices described herein can be used to induce fluid flow, optionally in conjunction with mechanical loading of the target bone, to increase the rate of bone healing in large segmental defects. For example, if the subject is mobile, they can move or otherwise load the injured bone in conjunction with flow treatment by the bone fixation assembly or implant, which may improve patient outcomes. In some examples, the bone fixation assemblies or devices described herein can be used to induce fluid flow for the primary treatment of tissue or bone injuries in patients that are immobile due to multiple traumas (and thus mechanical loading is not possible).

Example 1

In a particular example, the functionality of a bone fixation assembly 100 performing the described functionality (e.g., inducing controllable flow of interstitial fluid within a bone fracture site without mechanically compressing the tissue) can be experimentally verified as follows. The assembled bone fixation plate 104 and control unit 106 can be tested for their performance to induce fluid flow and for their safety. The biocompatibility of the device, while being active, will also be tested in vitro.

To examine the bone fixation assembly's 100 ability to induce fluid flow, the fabricated bone fixation plate 104 and packaged control unit 106 can be submersed in a simulated body fluid (to mimic the electrical conductivity of interstitial fluid) with silica powders added. The bone fixation plate 104 can be secured to a 3D-printed model of a rat's bone fracture, and a set of magnets (e.g., magnets 110) can be placed at a perpendicular orientation from the electrodes 108 (e.g., as shown in FIG. 3). A particle image velocimeter can be used to track the flow of the liquid and quantify its flow rate.

EM force is linearly proportional to the magnitude of the electric current and magnetic field. Therefore, the electric current and magnetic field will be varied to determine settings that can produce flow rate from about 3 to about 10 μm/s. Biomechanical regulatory models have shown that fluid flow in the range of about 3 to about 10 μm/s is most conducive to bone regeneration, with 3 μm/s being the minimum flow rate to cause cells to react and 10 μm/s or higher potentially resulting in detrimental effects. For purposes of this Example, 7 μm/s was chosen as the target flow rate.

The bone fixation assembly 100 will also need to operate at the specified levels of electrical current and magnetic field for implantation within a subject. The current is anticipated to be below 1 mA and the magnetic field anticipated to be 0.1 mT or less, which should produce the target flow rate.

To test the biocompatibility of the device, the bone fixation plate 104 and control unit 106 can be stored in standard culture media (e.g., DMEM). The electrodes 108 can generate a current for 20 mins daily, while a set of magnets 110 can be installed perpendicularly across the electrodes to induce EM fluid flow. The media can then be collected at 1, 7, and 28 days to culture L929 fibroblasts ($2\times10^4$ cells/cm$^2$) with 10% fetal bovine serum and 0.5% Penicillin-Streptomycin and incubated at 37° C. and 5% $CO_2$. Cell survival can be analyzed after 48 hours of exposure using Calcein-AM and ethidium bromide staining. Quantitative analysis of cell survival is expected to show no significant ($p<0.05$) differences in cell survival at any time points when compared to standard culture media, with cell survival greater than 95% for all time points.

Alternatively, if the biocompatibility of the implant does not reach a selected goal, the bone fixation plate 104 and control unit 106 can be coated with a layer of Parylene-C. Parylene is a commonly used conformal coating for many commercial implants and may further improve the biocompatibility of the implant.

The bone fixation assembly can be further evaluated to determine whether the drag force and fluid shear stress, not mechanical loading on the bone, are the key mechanotransduction stimuli for bone remodeling. A critical-sized bone defect (e.g., 6 mm) on a subject's (e.g., a rat) femur can be used as the model to test the hypothesis.

To evaluate the apparatus, a set of in vivo experiments can be conducted through a unilateral femoral defect model in subjects (e.g., Sprague Dawley rats) to determine the effects on subjects that have experienced fluid flow compared to the controls that have only experienced the electric current and magnetic field. Critical-size segmental bone defect on rats has been selected because it is a common model to study effectiveness of new implants and treatments for long bone fractures. In the described example, two groups (n=10 per group) of test subjects can be used. The numbers are based on previous research that uses the model to investigate the effect of mechanical loading, indicating 5-10 subjects per group should have significant differences in the designated outcome measures (mineral and vascular volumes, morphometric indices, mineral density).

The experimental group can be exposed to EM force-induced fluid flow for 20 minutes per day. The frequency and duration of the treatment are based on investigations showing that dynamic mechanical loading at this frequency and duration can generate a positive impact on bone regeneration. To exclude the potential effects of electrical current and magnetic field from the experiment, the experimental group can be compared to a control group that can also have the implant. However, instead of receiving the electric current and magnetic field simultaneously to induce fluid flow, the control group can experience the magnetic field for 20 minutes followed by electric current application of 20 minutes. There will be no fluid flow in the control group but the amount of electric current and magnetic field will be the same as the experimental group.

The bone fixation plate 104 can be implanted in 13-week old female Sasco Sprague Dawley. First, 6 mm bone defects will be surgically created on the test subject femurs, and stabilized with the bone fixation plate 104. The defects of all subjects can be treated with 2 μg rhBMP-2, delivered in a hybrid nanofiber mesh/alginate delivery system. Analgesia for the animals can be provided through sustained release of buprenorphine injection prior to surgery.

To generate the fluid flow, a harness, consisting of two opposing magnets (e.g., magnets 110), can be attached to the operated leg during treatment. Using Bluetooth communication, the user (e.g., via a remote-control unit) can instruct the control unit 106 to generate electrical current when the magnet harness is being worn (experimental group) or isn't (control group). As described above, the test subjects can be exposed to fluid flow of 7 μm/s for 20 minutes daily. To prevent damaging the harness or causing undue stress to the animal subjects, they can be anesthetized throughout the process. The rats can be sacrificed at the end of Week 8 using $CO_2$ asphyxiation.

The increase in level of bone regeneration with and without the active implant can then be quantified. To determine the effect of fluid flow on bone healing in the rat femoral implant model, a number of bone and vascular parameters can be evaluated from microCT imaging and histological examination of the subjects.

The vasculature of sacrificed rats can be perfused through the aorta, sequentially with saline with a vasodilator, neutral buffered formalin to fix the vessels, and finally a lead chromate-based radiopaque contrast agent (e.g., Microfil MV-122). MicroCT (e.g., using a VivaCT 40 device) images can be taken and segmented for bone and perfused vessels by application of a standard global thresholding and noise filtering technique. Following microCT imaging for bone and vessels, samples can be decalcified using a formic-acid based agent (e.g., Cal-ExII) for 2 weeks. The decalcified samples can then be imaged using identical settings and segmented for the remaining vascular anatomy.

For each sample, two volumes of interest (VOI) can be contoured for analysis. One volume will include the entire defect and surrounding soft tissue while the other will include only the nanofiber mesh and defect region, referred to as the "total VOI" and "defect VOI," respectively. The fixation plate can act as a reference for determining VOI locations. For pre-decalcification analysis, the volume of all attenuating tissues including bone and vasculature can be computed. After decalcification, various vasculature-related parameters can be assessed including vascular anisotropy, vessel thickness, thickness frequency distribution, volume, connectivity, and separation. The bone volume in the defect will be determined by subtracting the vascular volume from the pre-decalcified volume in the total VOI. To determine the uniformity of the healing response, vascular morphology between the proximal and distal ends of the defects can be compared by separately analyzing each half of the defect VOI.

Histologic samples can be fixed in 10% neutral buffered formalin for 48 h at 4° C. and then decalcified over 2 weeks under mild stirring on a rocker plate. 5 μm thick midsagittal sections can be cut and stained with Hematoxylin & Eosin and Safranin-O/Fast-green to provide qualitative assessments of bone healing and presence of cells and tissues associated with vascular and bone formation.

To ensure significance and validity of the results, a statistical power analysis can be performed to confirm the sample sizes used in this experiment to quantify bone and vascular formation. Mean mineral and vascular volumes and morphometric parameters such as thickness and spacing can be compared across the experimental and control groups, accounting for animal variability, via ANOVA with Tukey's post hoc analysis for pairwise comparisons. Statistical significance can be set at $p<0.05$, and data can be analyzed using, for example GraphPad Prism 5.0.

If insufficient difference is observed in the bone quality between the control and experimental groups, this may be caused by not finding the optimal fluid flow rate. In such a case, the flow rate can be increased to 10 μm/s and the treatment frequency to twice daily, compared to the original 7 μm/s per day.

Example 2

Referring to FIGS. 12-28, in a particular example, the functionality of a magnetohydrodynamics (MHD) pump system for stimulating FSS in vitro can be experimentally verified as follows. The MHD pump system 300 can generally comprise a continuous flow channel 302 (also referred to as a channel structure 302) coupled to a petri dish 304 (FIG. 13B) in which an electrically conducting fluid can be disposed, magnets (e.g., magnets 306), one or more electrodes (e.g., electrodes 308, FIGS. 16-17), an electrical power supply 310 (FIG. 18), and a supporting structure 312 (FIGS. 14-15)

The cell culture plate 314 (which can comprise the continuous flow channel 302 and the petri dish 304) can comprise an inlet port and an outlet port, through which medium (e.g., basal medium for supporting mammalian cell growth such as Dulbecco's Modified Eagles Medium (DMEM)) can flow allowing cells in the flow channel 302 to experience shear stress from the flow. The medium can be driven through the system using any of various methods.

In some examples, a mechanical pump can be used to drive the medium through the system, e.g., generating laminar flow for up to 24 hours. However, when used in vitro, this technique can produce high pressure at the inlet and the formation of air bubbles, which create non-FSS effects that alter the biochemical and biomechanical environment of cells. Another frequently used approach is the method of applying FSS by placing well plates on a rocking platform. This approach is simple, allows for long-term use, and provides high throughput of samples. However, this technique can only produce small magnitudes of FSS and has a non-uniform flow profile that is difficult to control. A 3D perfusion bioreactor is another approach that creates FSS in a porous scaffold by forcing fluid through it. This method generates a uniform flow profile inside a 3D construct, but the shear stress generated using this system is low when compared to the requirements of specific cells such as bone cells. In addition, shear stress using this method may arise from the strain and compression of the scaffold and not directly from the fluid flow. This complicates the accurate determination of FSS for comparison and evaluation.

To prevent or mitigate these issues, the flow system herein described comprises a magnetohydrodynamics (MHD) based pump to generate FSS in vitro without mechanical stimulation. FIG. 12 illustrates an exemplary MHD pump system 300 comprising a cell culture plate 314, one or more electrodes 308, and first and second magnets 306.

The MHD pump is configured to generate liquid flow due to the application of an electric field across a channel while under a DC magnetic flux that is orthogonal to the electric field. The orthogonally applied electric field and magnetic flux create Lorentz force, expressed in Equation (1), that moves electrically conductive particles (such as body fluid) in the direction orthogonal to both the electric field and magnetic flux.

As shown in FIG. 12, the MHD pump system 300 uses this force to create fluid flow along the channel 302, eliminating the use of moving mechanical parts. As indicated in Equation (1) above, the magnetic flux density and electric field intensity determine the velocity and direction of flow, which means that the flow rate can be controlled by varying either the magnetic flux or the electric field across the electrodes. MHD pumps have several advantages over other types of pumps, including the absence of moving parts, simple flow control, compatibility with a closed-loop flow system, and ease of fabrication and miniaturization. As shown in FIG. 3, in some examples, the magnetic flux flow can be upward in the orientation shown in FIG. 3, as represented by arrows 316, the current can flow in the direction represented by arrow 318, and the fluid can flow in the direction represented by arrow 320.

In vitro experiments using the system 300 above resulted in a promotion of fibroblast cell migration due to the application of FSS. The MHD pump system 300 enables the generation of uniform and controllable fluid flow over 2D cultured cells. In addition, unlike the other methods mentioned above, it is easier to incorporate this system into an implantable device (e.g., a bone fixation assembly such as the examples shown in FIGS. 1-3 and 5-8 and described with reference thereto) that will allow the study of fluid flow and FSS on certain cell responses. The ability to accurately study and determine the effects of electrical and mechanical cues both in vitro and in vivo advantageously leads to greater understanding of cell responses in normal and diseased conditions, which can consequently improve treatment outcomes of many diseases.

FIGS. 13A-13B illustrate an example of the cell culture plate 314. The cell culture plate 314 can comprise a continuous flow channel 302 (also referred to as a channel structure) including an outer wall 322 and an inner wall 324 coupled together via one or more struts/supports/members 326. Though the illustrated example shows only a single channel, in other examples the channel structure 302 can define any number of channels. The walls 322, 324 can comprise one or more slots/openings/recesses 328 configured to retain one or more electrodes 308 (FIGS. 16-17). The illustrated example includes two slots 328, however, in other examples the channel structure can comprise a greater or fewer number of slots. In the illustrated example, the slots have a substantially rectangular shape corresponding to the shape of the electrodes 308 (FIGS. 16-17), however, in other examples the slots 328 can have any of various shapes corresponding to the shape of the electrodes 308. The channel structure 302 can be coupled to a petri dish 304 as shown in FIG. 13B.

In a particular example, the continuous flow channel 302 can have an outer dimension of about 62.65 mm in length and about 47.5 mm in width with an internal width of about 5.5 mm. The slots 328 can have dimensions of about 7 mm by about 1.25 mm by about 8 mm and can be disposed in the walls of the channel, as shown in FIG. 13A. In some examples, the channel structure 302 can be manufactured using 3D printing, as described in Example 4 below.

Referring again to FIG. 12, the magnets 110 can be, for example, neodymium magnets. In the illustrated example the magnets have a trapezoidal prism shape, however, in other examples the magnets can have any of various shapes. In some particular examples, the magnets can have a base dimension of about 50.8 mm by about 50.8 mm, a top dimension of about 25.4 by about 25.4 mm, and a height of about 25.4 mm. The shape of the magnets 110 can concentrate the magnetic flux towards the electrode region and maximize magnetic flux intensity, leading to higher magnetic flux.

Referring to FIGS. 14-15, the MHD pump system 300 can comprise a support structure 312 configured to support and position the magnets parallel to each other. As shown in FIG. 14, the support structure 312 can comprise a main body 330 comprising a first magnet opening 332 configured (e.g., sized and shaped) to receive the first magnet 306, a support member 334 extending from the main body 330 (e.g., upwardly in the orientation shown in FIGS. 14-15), and an extension 336 comprising a second magnet opening 338 configured to receive the second magnet 306. FIG. 15 illustrates the support structure 312 with the magnets 306 disposed therein.

In some examples, the support structure 312 can be a 3D printed platform (e.g., fabricated on a LulzBot Taz 5 printer using a chroma strand black ABS filament). The magnets can be placed opposite each other with a separation distance of about 27 mm. The magnetic flux strength between the magnets 306 can be characterized by computer simulations performed using finite element method magnetics (FEMM)

with an axisymmetric magnetics model setup and a prescribed A boundary type which uses the Neumann boundary condition. The magnetic flux strength between the magnets was also measured experimentally using a gauss meter (e.g., a model GM2 AlphaLab, Inc. gauss meter).

To assemble the MHD system 300, one or more electrodes 308 (FIGS. 16-17) can be inserted into corresponding slots 328 (FIG. 13A) in the channel structure 302. In some examples, the electrodes 308 can be manufactured as described in Example 5 below. In the illustrated example, there are two slots 328, each of which receives an electrode 308. However, in other examples, the system 300 can comprise a greater or fewer number of electrodes. The cathode and anode electrodes can be respectively connected to the negative and positive terminals of a power supply (e.g., a KEPCO ABC 10-10DM programmable power supply). Electric current across the cell media can be measured, e.g., using a multimeter such as a Keithley 2001 Multimeter. While Lorentz force was previously described as a result of interaction between magnetic flux and electric field (see Equation (1)), in some examples, electric current can be measured instead of the electric filed due to the convenience in its measurement process. In such cases, assuming a uniform field distribution, the electric field E (V/m) across the flow channel can be determined using the following equation:

$$E = -Id/\sigma \qquad \text{Equation (2)}$$

where I is the electric current (A), d is the spacing between the electrodes (m), and $\sigma$ is the liquid conductivity ($S\ m^{-1}$).

Figure 18:
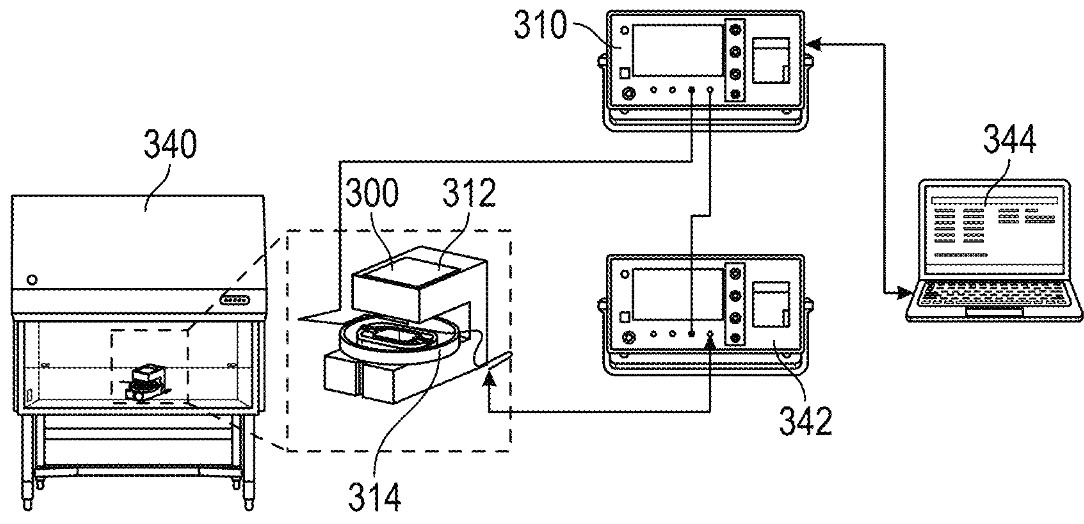
FIG. 18 illustrates the MHD system of FIG. 12 coupled to a power supply, multimeter, and control unit.

Referring to FIG. 18, the assembled cell culture plate 314 (including the channel structure 302 and electrodes 308) can be disposed between the two magnets 306 within the support structure 312 and the cathode and anode electrodes 308 can be connected to the power supply 310. As shown, the MHD system 300 can be disposed in a biosafety cabinet 340. The MHD system 300 can be further coupled to a multimeter 342. The power supply 310 can be coupled to a control unit 344 (e.g., a computer, smartphone, tablet, remote control, etc.). In some examples, a custom program can be used to control the system and record the measured current through a General-Purpose Interface Bus communication protocol. A pulsed DC input can be provided to the pair of electrodes 308 and the corresponding current can be measured. A pulsed voltage advantageously reduces current flow back (something which can occur when using a continuous output).

To validate the electric current and fluid velocity, the channel 302 can be filled with basal medium (e.g., Dulbecco's Modified Eagle's Medium (DMEM)). An input voltage with a pulsed amplitude cycle of turning on for 2 s, followed by turning off for 0.5 s can be applied. For each voltage value, the validation can occur for a total of 20 minutes, and the corresponding current across the electrodes can be recorded. The flow rate can then be determined by timing the amount of time it took for a marker (e.g., a floating, 0.2 mm polyvinyl chloride bead) to move 5 mm through the channel 302.

Prior to use of the channel structure 302 in the MHD system 300, cells can be disposed within the channel structure 302 (e.g., by seeding). The cells can be cultured in the channel 302, for example as described in Example 6 below.

Once the channel structure 302 has been seeded with cells, the examples of the MHD system 300 described herein can be used and validated in the manner described in Example 3 below.

The in vitro MHD system 300 generates fluid flow over cells and has been advantageously shown to enhance the migration of cells into a wound area. The MHD system 300 can be used as an in-vitro device to model wound healing as well as to study and quantify FSS for other diseases. This system can lead to better outcomes in many medical therapies because understanding the role of shear stress on cell function and regulation is crucial to the development and improvement of these therapies. The study of FSS will also provide important information in tissue engineering and development of functional tissue constructs. Moreover, this technology can be adapted for in-vivo devices, such as bone fixation assemblies 100, 150 described previously, and bandage device 200, which allows for further study of diseases with in vivo models that are more relevant to the real-world conditions.

Example 3

The examples of the MHD system 300 described herein can be used and validated in the following experimental manner. Fibroblast cells can be seeded on a custom cell culture setup and can be subject to a DC electric field and magnetic flux to study the effects of both electricity and FSS on fibroblast migration.

The experiment can be divided into four groups of three samples each. The experimental groups include a control group (no electric field or magnetic flux/field), an electric field only group, a flow group (with both magnetic flux/field and electric field) with relatively low electric field, and a flow group (with both magnetic flux/field and electric field) with relatively high electric field. The electric field only group had a 0.4 V of DC applied. For the flow groups, the magnetic flux/field at the center of the channel was 0.5 T, and the DC voltage was 0.4V and 0.7V for the low electric field and the high electric field respectively. Using Equation (2) (as defined above), the theoretical electric field inside the flow channel is calculated to be 1.9 $mV\ cm^{-1}$ (input voltage=0.4V) for the electric field only and the flow group with low electric field. In comparison, the high flow group was subject to an electric field of 10.8 $mV\ cm^{-1}$ (input voltage=0.7V). There was a 5-fold increase in electric field when the input voltage changes from 0.4V to 0.7V due to the non-linear increase in the generated current densities between these voltages.

Figure 19:
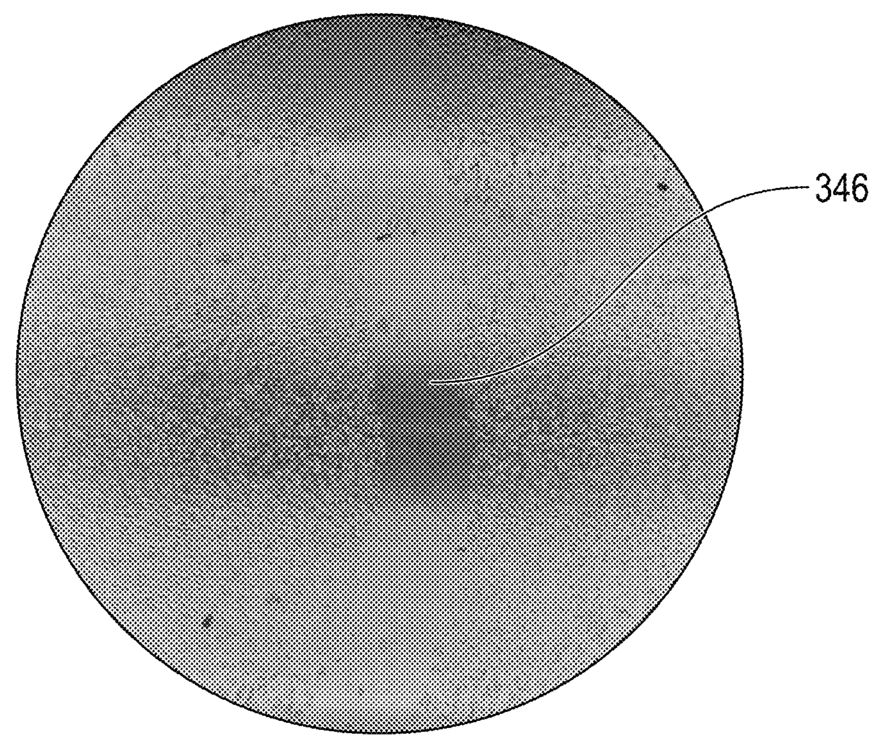
FIG. 19 is an image of a scratch created on a confluent cell layer.

As shown in FIG. 19, a scratch assay (e.g., following a protocol by Martinotti S and Ranzato E2019 Scratch wound healing assay in Epidermal cells. (Berlin: Springer) 225-9) was implemented to create a wound 346. Briefly, cells can be seeded into the channels of the respective modified culture plates at a density of $5\times10^3$ cells/$cm^2$. Cells were incubated at 37° C. in a humidified $CO_2$ incubator (5%) for 24 hours. After checking for a uniform monolayer of cells, a scratch 346 was created perpendicular to the electrodes using a 200 μL pipette tip (see FIG. 19). Subsequently, cell media can be replaced with fresh media. Following that, treatment, which either consists of no field, electric field only, or both electric field and magnetic flux/field, was administered for 20 minutes per treatment group. Treatment was repeated every two hours for a total of 100 minutes over 12 hours. The samples were put back into incubation between each treatment. Cells were imaged using a phase-contrast microscope to observe migration of cells towards the scratch created. Images at a time point of 12 hours from the wound creation were used to quantify the migration rate. The 12-hour time point was selected as a reasonable time to determine the effectiveness of the experiment because 8-18 hours is the time window expected for cells to fill in a scratch/wound area.

Cell migration was quantified using ImageJ from the NIH (v1.53q). The images were analyzed by comparing the area covered by cells following treatment across all groups. Migration rate, M, was specified as the percentage of the wound area covered with migrating cells at a specific time and is described by Equation (3):

$$M(t) = \frac{A(t)}{A(0)} \times 100\% \quad \text{Equation (3)}$$

Where A(t) is the area covered with cells at time t and A(0) is the wound area at the beginning of the experiment. To make the analysis consistent, phase-contrast images were first filtered with a bandpass filter and then area output was extracted by outlining the areas with no cells.

Statistical analysis was done using ANOVA and a t-test on Microsoft Excel for the 12 h time group while the 7 h time group was analyzed using Welch ANOVA and Games Howell post-hoc test using Python 3.8. P-values less than 0.05 were considered significant.

Figure 20:
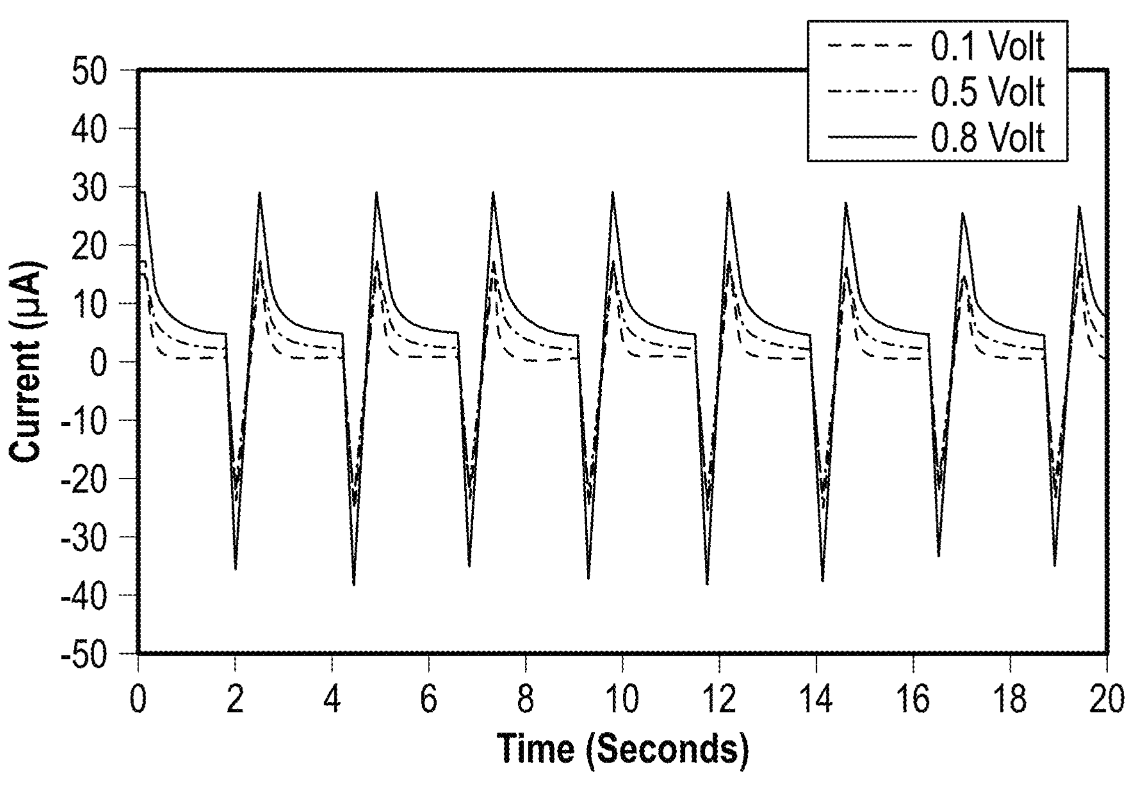
FIG. 20 is a chart illustrating the current density generated with applied pulsed voltage.
Figure 21:
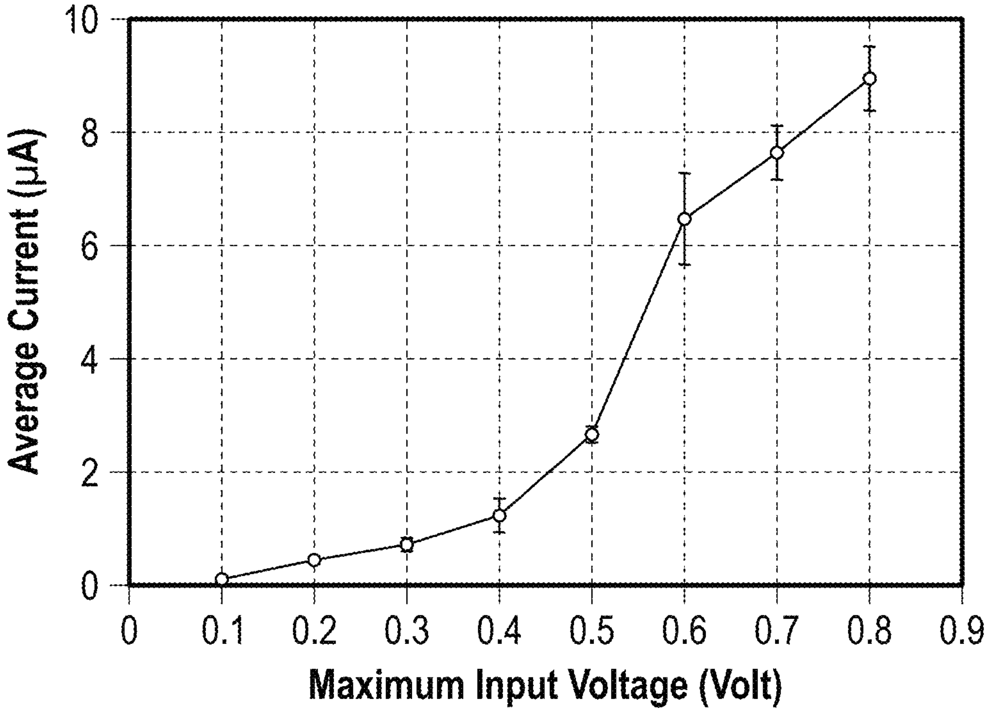
FIG. 21 is a chart illustrating the average current as a function of the maximum input voltage.

Characterization of the current across the channel when using DMEM media with a conductivity of 1.4 S/m showed a linear relationship between the input voltage and current generated. For the channel dimension and electrode used, the current density is shown to increase with input voltage, see FIGS. 20-21. In addition, the voltages used (<0.8 V) were below the threshold of hydrolysis reaction, as evident from no observation of bubbles and the consistent current profile over many cycles of voltage pulses. This is important because hydrolysis reactions on electrode surfaces could lead to degradation of the electrode surface, thereby reducing the current generation over time. The observed oscillation in the current recorded is due to the use of a pulsed voltage source. FIG. 20 illustrates the current density generated with applied pulsed voltage with maximum voltage of 0.1 V, 0.5 V, and 0.8 V. FIG. 21 illustrates the average current as a function of the maximum input voltage, (n=3, error=±standard deviation).

Figure 22:
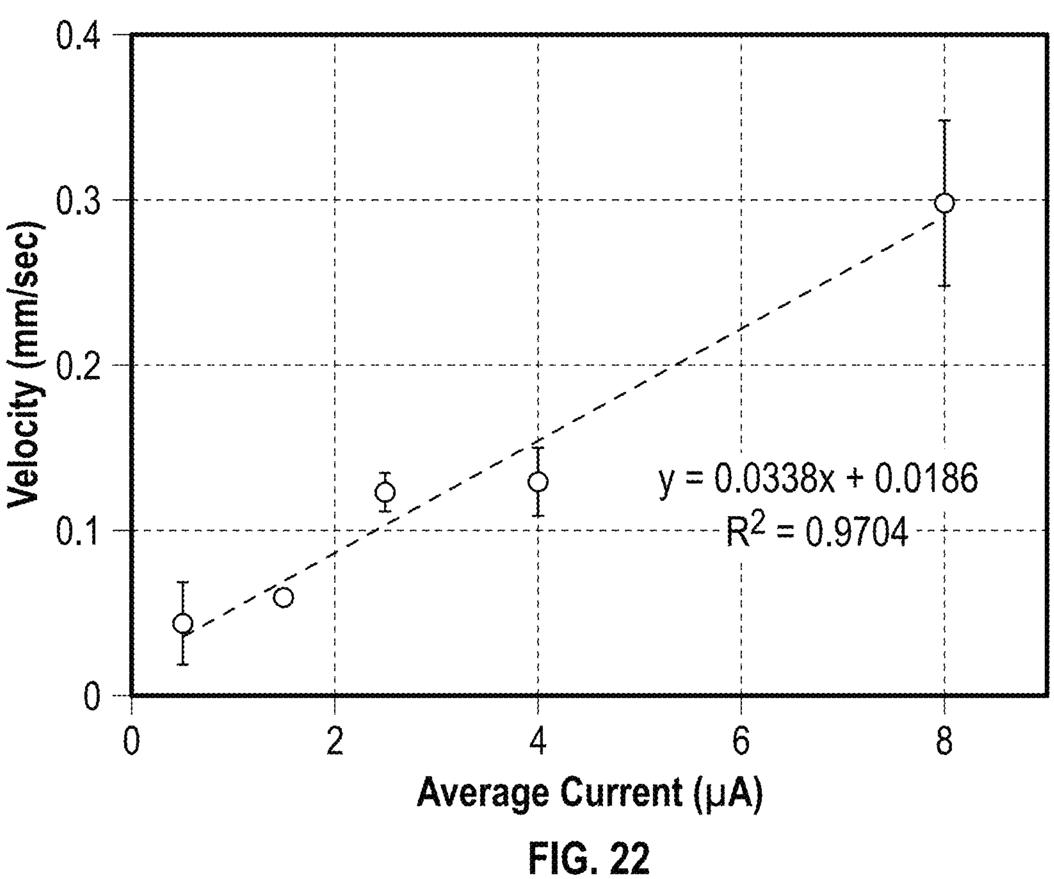
FIG. 22 is a chart illustrating the fluid velocity measured for corresponding average current measured between the electrodes.

When the flow channel was subjected to the magnetic flux/field and a pulsed input voltage with a cycle of turning on for 2 s followed by turning off for 0.5 s, fluid flow was observed in the channel. FIG. 22 plots the corresponding velocity profile in the channel with respect to the current measured across the electrodes. The flow velocity increases with the current amplitude with good linearity. Due to the use of pulsed voltage, the MHD pump can exhibit a reverse flow period that occurs towards the end of the magnetic flux. This can complicate the fluid velocity measurement, which is performed by observing the motion of a floating bead over time.

Figure 23:
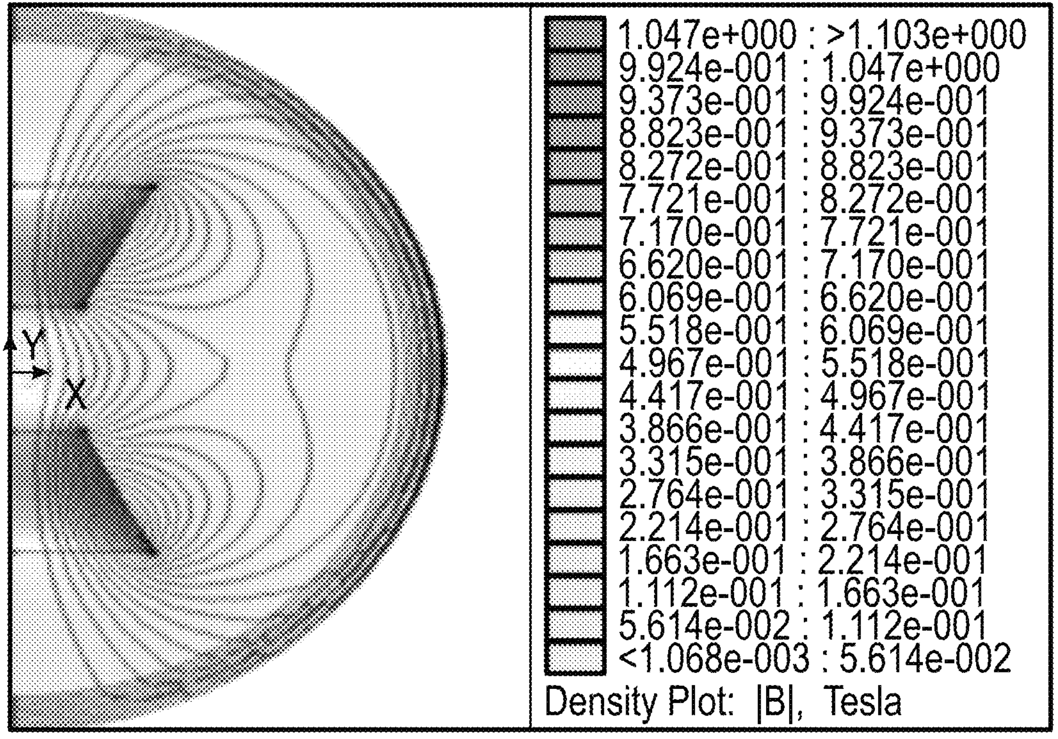
FIG. 23 is an FEMM simulation output showing magnetic flux density.
Figure 24:
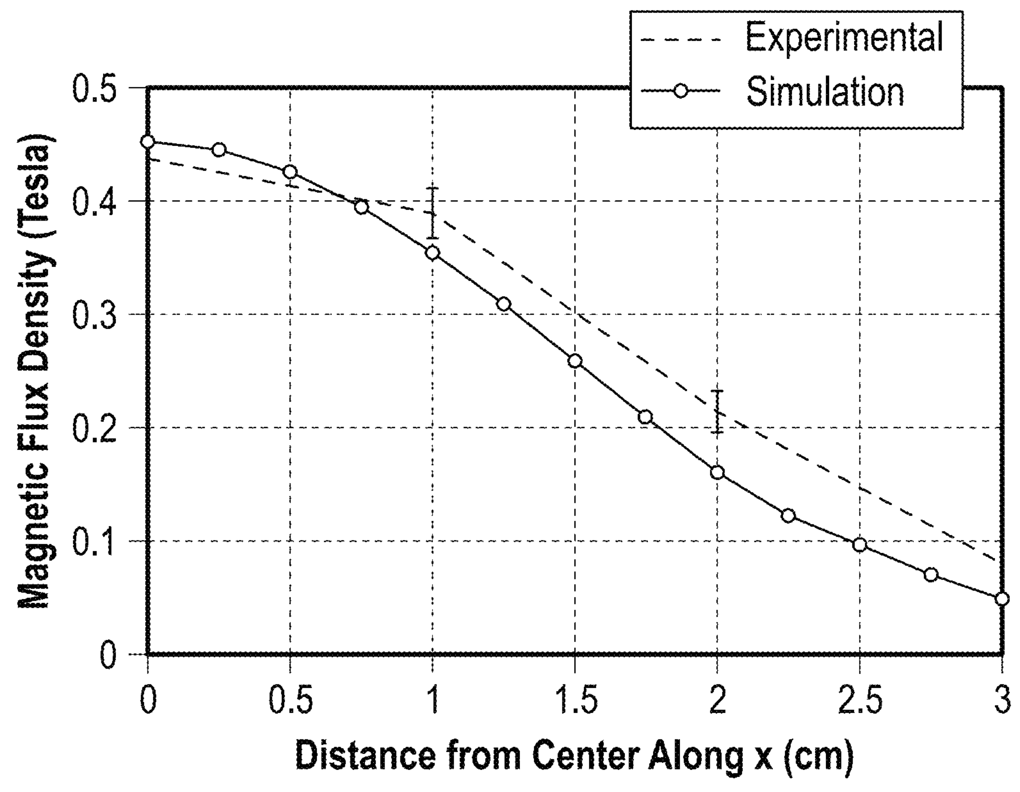
FIG. 24 is a chart illustrating the magnetic flux density between the magnets when simulated and experimentally.

As previously described, trapezoidal prism-shaped magnets were placed opposite to each other to maximize the magnetic flux intensity at the center where the electrode region resided. Finite Element Method Magnetics (FEMM) simulation shows that the trapezoidal prism shape has an improved magnetic flux concentration with respect to the electrode region. FIG. 23 shows an FEMM simulation output showing magnetic flux density. Results show a good agreement between numerical simulation and experimental measurements collected with a gauss meter. FIG. 24 shows the magnetic flux density between the magnets when simulated and experimentally.

Shear stress in a rectangular channel is affected by the medium's flow rate and viscosity, as well as the channel's height and width. Assuming flow in the channel to be steady, incompressible, and Newtonian, the shear stress for a channel can be approximated using Navier-Stokes equation. The flow is considered to be a Couette flow and shear stress is calculated using Equations (4) and (5):

$$\tau = 2\mu Q/wh\verb|^|2 \quad \text{Equation (4)}$$

$$Q = vwh/2 \quad \text{Equation (5)}$$

where τ is the wall shear stress in Pa, μ is viscosity in Pa*s, w is the width of flow channel in m, h is the channel height in m, and v is average velocity in m $s^{-1}$.

Figure 29:
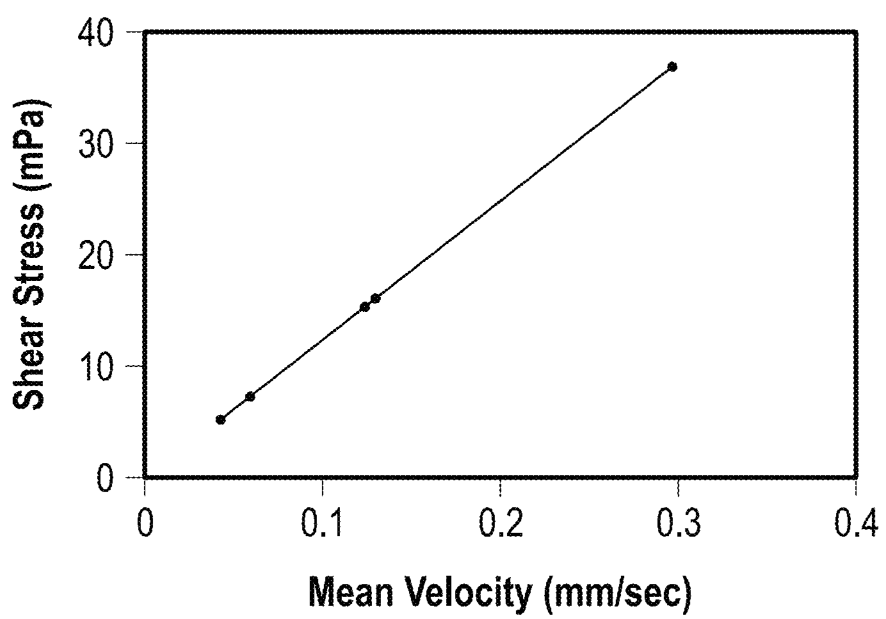
FIG. 29 is a chart illustrating the shear stress generated by the system as a function of average velocity.

Using equation (4), the range of fluid flow-induced shear stress generated by the system during the experiments was calculated to be between 4.2 μPa and 28 μPa for DMEM with 0% FBS and between 5.3 μPa and 36 μPa for DMEM with 10% FBS which was used for cell culture experiments. FIG. 29 plots the shear stress generated by the system as a function of average velocity. It should be noted that the shear stress is directly related to volume flow rate and the range of shear stress can change if magnetic field is increased without changing the amount of electric field. Furthermore, changing the channel design and specially the height of the channel will allow for customizing the system to deliver lower or higher shear stress values.

Figure 25:
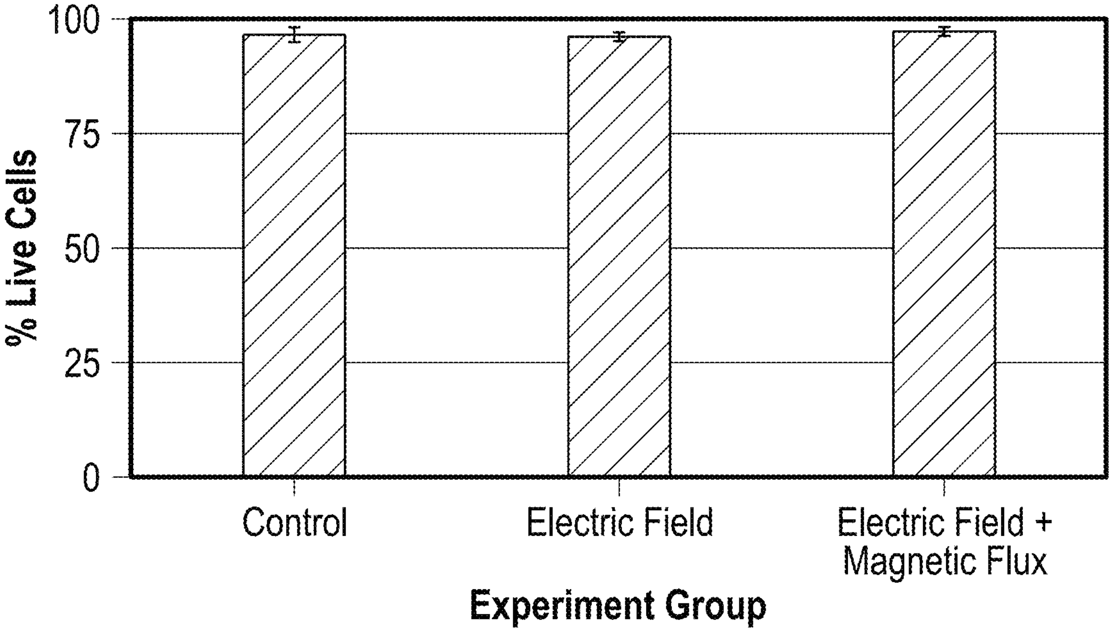
FIG. 25 is a chart illustrating the percentage of live cells relative to the number of total cells across experiment groups.

The MHD system 300 was shown to be biocompatible for the L929 fibroblast cells. FIG. 25 plots the viability of cells following treatment using a live dead assay, and shows the percentage of live cells relative to the number of total cells across experiment groups (n=2, error=±standard deviation). The data shows that there was no significant difference between the control and experimental groups which consisted of an electric field only and the combination of an electric field and magnetic flux treatment groups. A one-way ANOVA statistical analysis showed no significant difference between the experimental groups with a p-value of 0.739. This shows that the current level and the techniques used with this system setup are biocompatible to the cells.

Figure 26:
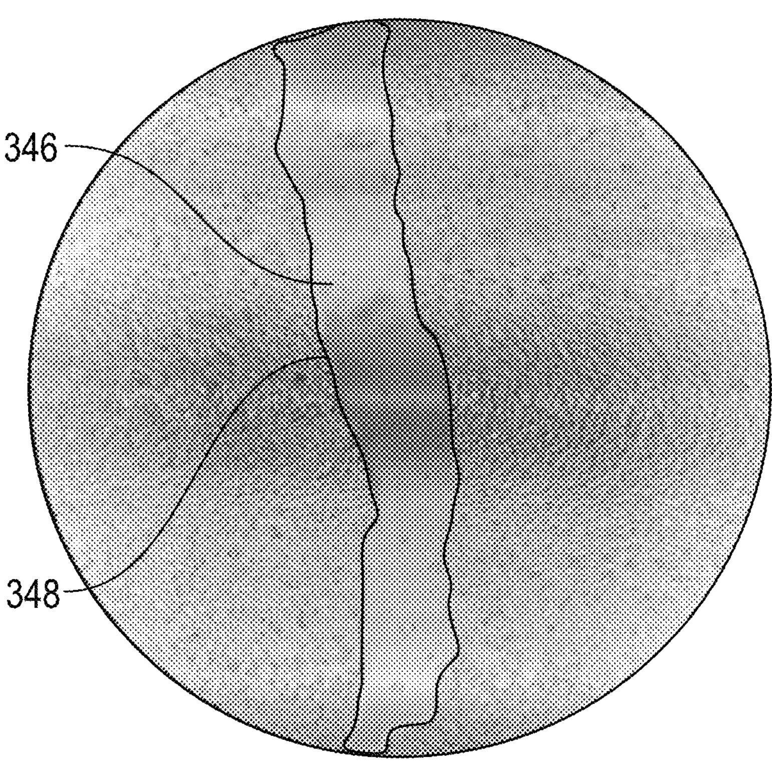
FIG. 26 is an image showing the relative wound coverage of the flow group (electric field and magnetic flux) at t=0.
Figure 27:
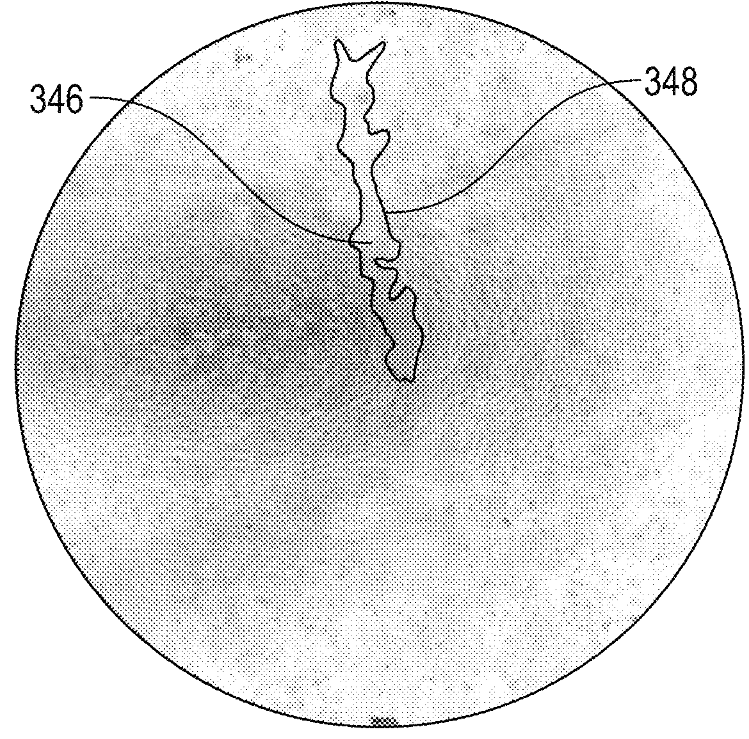
FIG. 27 is an image showing the relative wound coverage of the flow group (electric field and magnetic flux) at t=12 hours.
Figure 28:
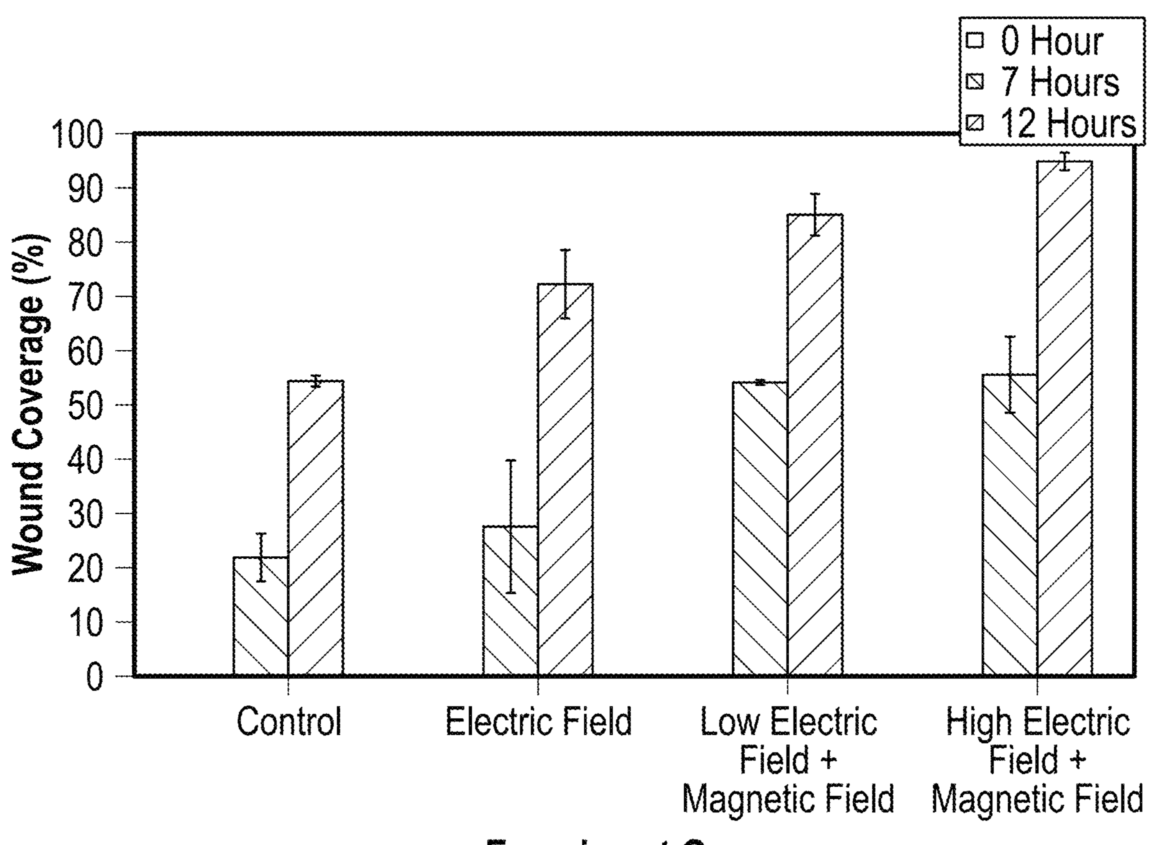
FIG. 28 is a chart illustrating the percentage of wound coverage at t=0, 7, and 12 hours for the control, electric field, and the electric field and magnetic field group.

Results show that application of electric field across the electrodes promotes movement of cells to the manual wound created on a cell monolayer, up to 44% compared to the control (no electric field or magnetic flux/field). The electric field only group showed enhanced migration compared to the control group, indicating that the migration is a result of electrotaxis. This is consistent with research on how a DC electric field influences cell orientation, movement, and migration velocity in vitro. In contrast, MHD-generated fluid flow (due to application of both electric field and magnetic flux) increased wound coverage by 90% compared to the control group ($p<0.01$) depending on the input voltage applied, as indicated in FIG. 28. This is a clear indication that the additional increase in wound coverage (from improved cell migration) was due to the fluid flow. FIG. 26 illustrates the wound 346 coverage (the edge of the wound is outlined by line 348) at time t=0 and FIG. 27 illustrates the wound coverage at time t=12 hours (for the input voltage=0.4V flow group). FIG. 28 is a plot showing the percentage of wound coverage at t=0, 7, and 12 hours for the control, electric field, the low electric field and magnetic field group, and the high electric field and magnetic field group (n=3, error=±standard deviation). The low electric field group was exposed to an electric field of 1.9 v $cm^{-1}$ (input voltage=0.4V), resulting in an estimated 0.059 mm $s^{-1}$ flow rate across the channel. The high electric field group was exposed to an electric field of 10.8 v $cm^{-1}$ (input voltage=0.7V), resulting in an estimated 0.29 mm $s^{-1}$ flow rate across the channel.

The effect of a static magnetic flux/field on the behavior of cells is negligible as reported in the literature. It has been highlighted that a magnetic field of above 4T is needed to influence cell orientation depending on cell type. Moreover, it has been shown that magnetic flux/field of only up to 10 T is necessary to produce proliferation effects on human fetal lung fibroblast cells. The magnetic flux/field used on this system is much lower with a maximum field of 1-1.1 Tesla (FIG. 24). Therefore, the migration effects observed in these experiments are attributed to the applied electric field and fluid flow-induced shear stress.

Example 4

In some examples, the channels 302 can be 3D printed via a stereolithography printer (e.g., a Formlabs 2 printer) using Surgical Guide resin (e.g., Formlabs surgical guide resin). Following that, the channels can be washed for 20 minutes in 99% isopropyl alcohol (IPA) and cured using ultraviolet (UV) light for 30 minutes at 60° C. Next, the channels 302 can be washed in an ultrasonic washer for 5 minutes with deionized (DI) water and surgical soap followed by DI water and then IPA. The channels can then be autoclaved at 121° C. for 30 minutes to remove any residual resin. The autoclaved channels can then be coupled/attached to a 100 mm petri dish (e.g., a Dow Corning petri dish) using, for example, biocompatible curable epoxy (e.g., Dymax 1072-M UV curable epoxy). Finally, vertical slots of about 15 mm can be created on the walls of the assembled petri dish 304 to aid electrode wire placement and ensure proper closure of the lid during the experiment.

The modified plate 314 (FIG. 13B), can then be washed in the ultrasonic washer for 5 minutes in a solution of surgical soap and DI water, then 5 minutes in DI water alone, and followed by 2 minutes in IPA to remove any uncured epoxy. Following washing, the plates can be coated with Parylene-C using a vapor deposition system (e.g., a PDS 2010 Labcoater). The coated plates can then be etched using a plasma etching system (e.g., a March Jupiter II RIE system) to create a surface that is conducive to cell adhesion. In some examples, the etching can be performed for 30 seconds using 100-watt power. The plasma-treated plates can then be sterilized by soaking in ethanol for 10 minutes followed by 30 minutes of UV light exposure.

In some examples, any of the above-described steps of the manufacturing method can be optional, and the described steps can be performed in any order.

Example 5

In some examples, electrodes 308 can be fabricated using 1 mm thick commercially available glass slides (e.g., Thermo Fisher Scientific slides). The glass slides can be cut into about 6 mm by about 9 mm pieces using a glass cutter to become substrates for electrodes. The glass substrates can be cleaned using a sequential step of acetone, DI water, and IPA sonication. Each step can be performed for about 5 minutes to ensure that the glass surface is clean and to remove any residue on the surface that may reduce the quality of the electrode surface. Following that, the substrates can be plasma etched using a plasma etcher (e.g., a MARCH plasma etcher) for 60 seconds at 100 Watts on each side. After the substrates have been etched, electrodes can be fabricated by depositing metals onto the substrate using, for example, a vapor deposition system (e.g., an AMOD Physical Vapor Deposition system) to create a conductive electrode surface. The fabrication process can begin by first depositing a 10 nm titanium layer to create a strong adhesion layer. Following that, a 200 nm layer of platinum can be deposited.

As shown in FIG. 17, the electrodes 308 can be attached to 22 gauge conducting wires 350 using epoxy (e.g., an 8331D conductive silver epoxy) to create an electrical connection between the wire 350 and the electrode 308. The wire 350 and electrode 308 can then be heated at 65° C. for 10 minutes to ensure that the wire is fully cured onto the electrode. The conductive epoxy can then be sealed, for example, using a curable epoxy (e.g., Dymax 1072-M UV curable epoxy). This avoids contact between the cathode and anode electrodes and encapsulates the non-biocompatible silver epoxy. Electrodes with attached wires can then be sterilized with a 2-minute ethanol soak followed by 30 minutes of UV exposure.

In some examples, any of the above-described steps of the manufacturing method can be optional, and the described steps can be performed in any order.

Example 6

Cells (e.g., L929 fibroblasts) were cultured within the channel structure 302 using the following method. The cells were maintained in a standard culture medium composed of 10% fetal bovine serum (FBS) and 1% penicillin/Streptomycin in DMEM. Modified plates including the channel structure 302 were treated with 1% gelatin by coating the bottom surface of the plates in the gelatin solution for 45 minutes and incubating at 37° C. to improve cell adhesion inside the channel structure 302. To ensure that the technique and experiment setup were safe for cells, the viability of cells was tested using a live dead assay. L929 fibroblast cells were seeded at 20,000 cells/$cm^2$ on the fabricated culture plates. Treatment (e.g., application of an electric field, magnetic field/flux, or both) was applied to each culture plate after cells were observed to be confluent. Following the treatment, all culture plates were stained using e.g., Calcein-AM and Ethidium homodimer-1 and imaged using a microscope such as the Agilent Cytation 5 microscope. Finally, the percentage of live cells was quantified, e.g., using ImageJ.

Example 7

Figures 38, 39A, 39B, 39C:
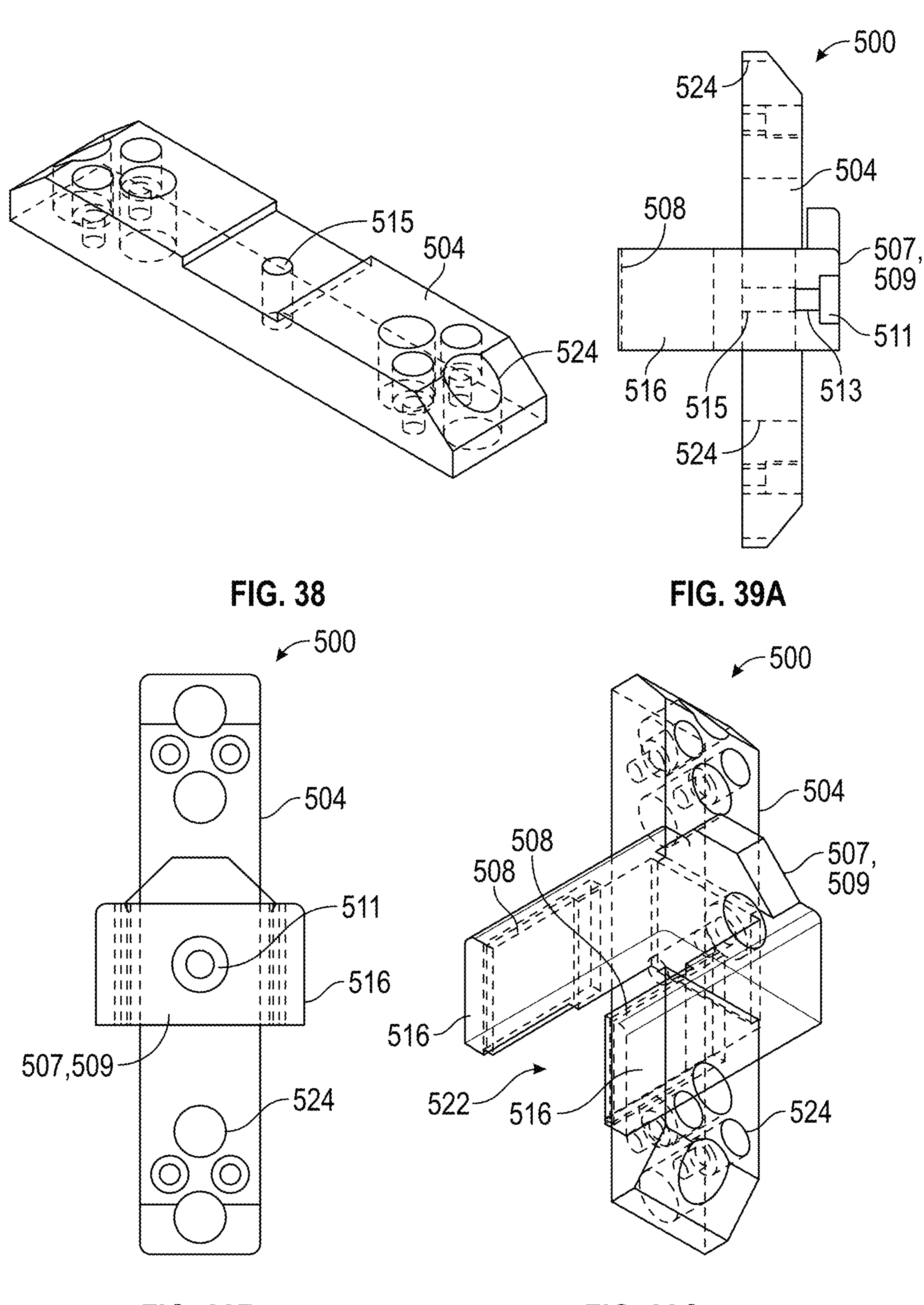
FIG. 38 is a perspective view of a bone fixation plate of a bone fixation assembly.
FIG. 39A is a side view of a bone fixation assembly which includes the bone fixation plate of FIG. 38 coupled to an electrode module containing the electrodes.
FIG. 39B is a front view of the bone fixation assembly of FIG. 39A.
FIG. 39C is a rear perspective view of the bone fixation assembly of FIG. 39A.
Figures 40, 41:
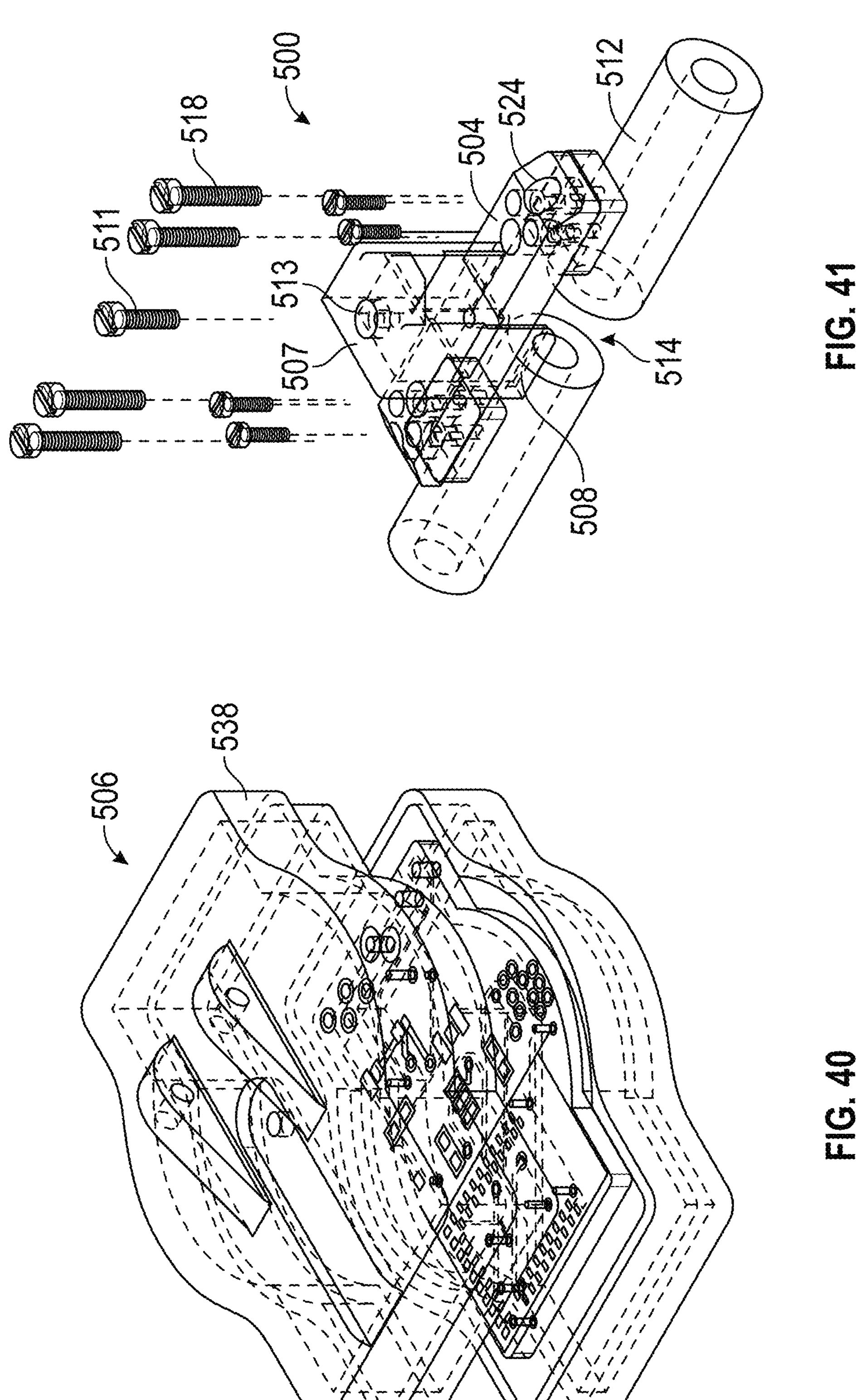
FIG. 40 is a perspective view of a control unit for the bone fixation assembly of FIGS. 39A-39C.
FIG. 41 is an exploded view of the bone fixation assembly of FIGS. 39A-39C coupled to a bone containing a fracture.

FIGS. 38-40 illustrate components of a bone fixation assembly 500 that was tested in vivo in rats. The bone fixation assembly depicted in FIGS. 38-40 may be the same, or similar to, the bone fixation assembly 100 described above with reference to FIGS. 1-3. Thus, the components of the bone fixation assembly shown in FIGS. 38-40 are labeled to correspond with those of bone fixation assembly 100 and are not redescribed below for the sake of brevity. For example, openings 524 can correspond to openings 124.

In particular, the bone fixation assembly 500 generally comprises a bone fixation plate 504 (shown alone in FIG. 38), an electrode module 507 couplable to the bone fixation plate 504 and containing the electrodes 508 therein (shown in FIGS. 39A-39C), a control unit 506 (shown in FIG. 40)

that controls and powers the electrodes 508, and one or more magnets 110 (as shown in FIG. 3, for example). In some examples, the coupled together bone fixation plate 504 and electrode module 507 can be referred to as an "implant" or "bone fixation implant."

The control unit 506 and the electrode module 507 are electrically coupled to one another via one or more wires, such as described above with reference to FIGS. 1-3 (e.g., via wires 118).

The electrode module 507 contains the electrodes 508 therein. For example, the electrode module 507 comprises a front body 509 that attaches to a central portion of the bone fixation plate 504 and extension members 516 which extend outward an away (in a same direction) from opposite sides of the front body 509. As such, the two electrodes 508 are spaced apart from one another and a channel 522 is formed between them, which is configured to receive the subject's bone 512 therein (at the location of the fracture 514), as shown in FIG. 41.

The electrode module 507 can be coupled to the bone fixation plate 504 by a fastener 511 extending through corresponding apertures 513, 515 in the electrode module 507 and bone fixation plate 504, respectively (as shown in FIGS. 39A-39C and 41).

The bone fixation plate 504 was disposed adjacent the subject's bone 512, at the fracture 514, as depicted in FIG. 41. As a result, the two opposing electrodes 508 extended across opposite sides of the fracture 514 in the bone 512. The bone fixation plate 504 was attached to the bone 512 by a plurality of fasteners 518 (e.g., bone screws) extending through corresponding openings 524 in the bone fixation plate 504.

Figure 42:
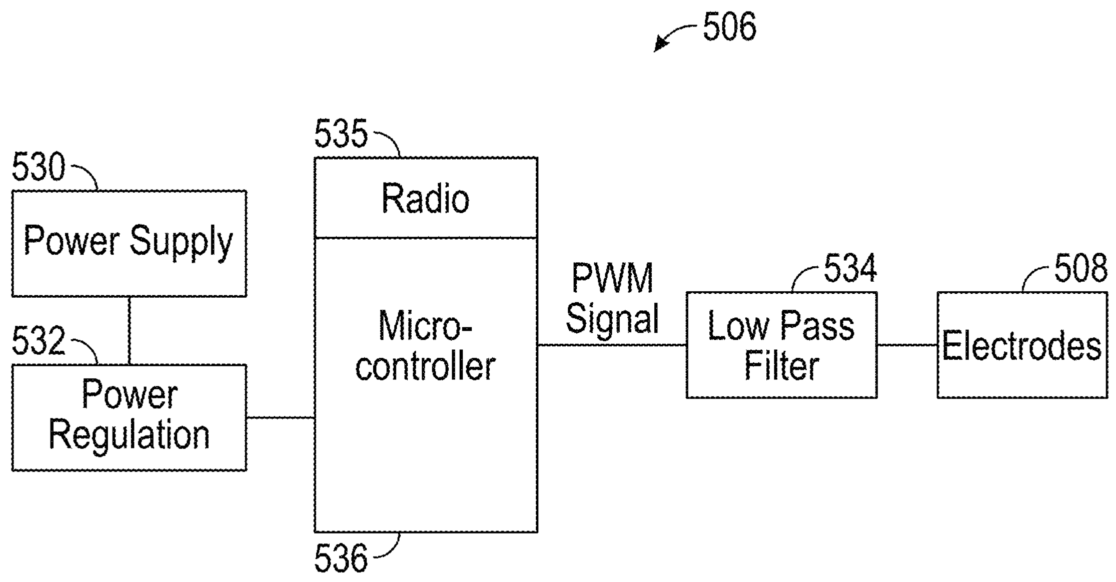
FIG. 42 is a system diagram of the control system of the bone fixation assembly of FIGS. 39A-39C, which includes the control unit of FIG. 40.

The control unit 506 can include the same or similar components to the control unit 106, as described above, including a microcontroller 536 (with radio 535), a power supply 530 (e.g., a battery), a power regulator 532, and a low pass filter 534 (as shown in FIG. 42), all enclosed in a housing 538 (as shown in FIG. 40). The power supply 530 was activated to provide voltage to the microcontroller 536, which sent a pulse width modulated signal through the low pass filter 534 and to the electrodes 508, thereby creating the electric field between the electrodes 508.

The magnets 110 (e.g., first and second magnets) were disposed externally to the subject, on a platform. However, for other experimental studies or treatments, the magnets 110 could be disposed externally to the subject, for example, on or within a harness/strap/bracelet/wrap/cast worn by the subject. The magnets 110 provided a magnetic field perpendicular to the flow direction of the electric current between the electrodes 508.

To evaluate the bone fixation assembly 500, a set of in vivo experiments were conducted through a unilateral femoral defect model in subjects (e.g., Sprague Dawley rats, wistar rats) to determine the effects on subjects that have experienced fluid flow (flow group) compared to the controls that have experienced no stimulation, the magnetic field only, or the magnetic field and electric field with no flow. The experiment followed the protocol described above, with reference to FIGS. 1-3 and bone fixation assembly 100.

The experimental flow group was exposed to EM force-induced fluid flow for 20 minutes per day, starting on the third day following surgery (e.g., implantation of the bone fixation assembly). To exclude the potential effects of electrical current and magnetic field from the experiment, the experimental flow group was compared to three no flow control groups that also had the implant. However, instead of receiving the electric current and magnetic field simultaneously to induce fluid flow, the control groups either experienced the magnetic field for 20 minutes followed by electric current application of 20 minutes ("MF+EF"), the magnetic field only ("MF only"), or no magnetic field or electric current ("no stimulation"). There was no fluid flow in any of the control groups.

Figure 43:
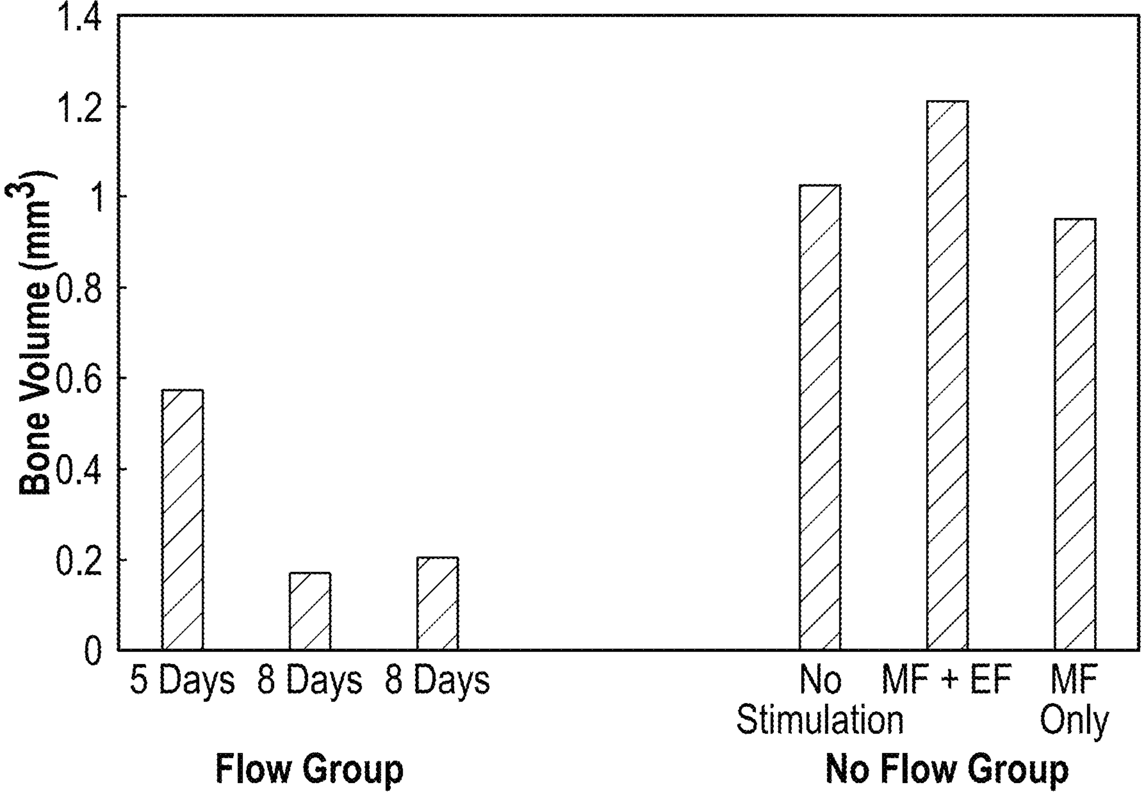
FIG. 43 is a chart illustrating the bone volume for a flow group and three no flow control groups for experiments conducted with the bone fixation assembly of FIGS. 39A-39C.

Various measurements were taken during the treatment with the bone fixation assembly 500, for both the flow group and the no flow control groups, including a measurement of bone growth over time. FIG. 43 shows a graph of bone volume ($mm^3$) for the three devices of the flow group at times points of 5 days, 8 days, and 8 days post implantation, respectively, for the three devices. The graph in FIG. 43 also shows the bone volume ($mm^3$) for the three no flow control groups described above, at a time point of two weeks.

The data observed during this study is comparable to studies that used mechanical loading to promote bone healing. Various studies have shown that early loading of the healing bone disrupts vessel formation and hinders the healing process. One study showed that a bone loaded right after fixation showed 75% decrease in bone volume compared to a group that was subjected to mechanical loading later.

Moreover, there are studies showing that magnitude of strain should be low in the early stage of healing and higher in the repair phase of healing to promote mineralization of the callus. Therefore, the decreased bone volume observed in the flow group is associated with the timing or the magnitude of shear stress, or both, induced at the fracture site.

To provide a positive effect on bone healing (e.g., increase bone regeneration at the earlier time point), optimizing the timing, frequency, and magnitude of treatment is important. For example, in the case of application in humans, the reparative phase starts at week two (post-surgery), and therefore external stimulations would be more beneficial at this stage. Thus, it is proposed that treatment begins at approximately two weeks post-surgery or post-implantation of the implant. In some examples, the treatment starting timepoint can be in a range of 14-21 days post-implantation or post-surgery.

As discussed above, the frequency of treatment can be 2-3 times per week, at least two times per week, at least three times per week, or 2-4 times per week. The duration of each treatment (each application of the electric field) can be 20 minutes (e.g., 20 minutes per treatment day), or in a range of 15-25 minutes, or 15-60 minutes.

Additional Examples of the Disclosed Technology

In view of the above-described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. An assembly for promoting interstitial fluid flow, comprising: an implant configured to be disposed at a selected site of a subject, the implant comprising spaced apart first and second electrodes; a control unit electrically coupled to the first and second electrodes, the control unit configured to provide power to the first and second electrodes to generate an electric field at the selected site; and one or more magnets disposed adjacent to the selected site, the one or more magnets configured to generate a magnetic field in a direction orthogonal to the electric field in order to drive interstitial fluid flow at the selected site.

Example 2. The assembly of any example herein, particularly example 1, wherein the selected site is a fracture in a subject's bone, wherein the implant and the control unit are implanted within the subject at the selected site, and wherein the implant is configured to be placed in contact with the subject's bone and span the fracture, with the first and second electrodes disposed on either side of the fracture.

Example 3. The assembly of any example herein, particularly either example 1 or example 2, wherein the one or more magnets are disposed in a wearable harness that is configured to be worn by the subject, external and adjacent to the selected site.

Example 4. The assembly of any example herein, particularly any one of examples 1-3, wherein the control unit is disposed on the implant.

Example 5. The assembly of any example herein, particularly any one of examples 1-4, wherein the control unit comprises a microcontroller, a power supply, and a power regulator, and wherein the control unit is connected to the first and second electrodes by wires.

Example 6. The assembly of any example herein, particularly example 5, wherein the control unit further comprises: relays which are configured to switch between sensing and stimulating modes, wherein in the sensing mode a signal from the first and second electrodes provides feedback as to a status of a tissue at the selected site as it heals, and wherein in the stimulating mode the first and second electrodes supply the electric field for generating the interstitial fluid flow; and a network analyzer which is configured to measure an impedance of the tissue at the selected site, between the first and second electrodes, for determination of the status of the tissue.

Example 7. The assembly of any example herein, particularly any one of examples 1-6, wherein the one or more magnets includes a pair of magnets that are placed at a perpendicular orientation relative to the first and second electrodes.

Example 8. A method of treating a subject in need thereof, comprising disposing the assembly of any one of examples 1 to 7 at the selected site and generating the electric field orthogonal to the magnetic field at the selected site for a predetermined duration of time.

Example 9. The method of any example herein, particularly example 8, wherein generating the electric field comprises applying pulsed input voltage to the first and second electrodes for the predetermined duration of time.

Example 10. The method of any example herein, particularly either example 8 or example 9, wherein the subject has a bone fracture, a laceration, or a shallow tissue injury at the selected site.

Example 11. The method of any example herein, particularly any one of examples 8-10, wherein the predetermined duration of time is in a range of 15-25 minutes, and further comprising generating the electric field orthogonal to the magnetic field at the selected site for the predetermined duration of time starting at 14-21 days following implantation of the implant at the selected site and at a frequency of two to three times per week.

Example 12. The method of any example herein, particularly any one of examples 8-11, further comprising switching from a stimulating mode where the electric field is generated by the first and second electrodes to a sensing mode where a signal from the first and second electrodes is obtained by the control unit and processed to determine an impedance of a tissue at the selected site for a determination of a healing status of the tissue.

Example 13. An assembly for promoting interstitial fluid flow, comprising: a bone fixation implant comprising: a bone fixation plate configured to be coupled to a bone of a subject at a location of a fracture; first and second electrodes that are spaced apart from one another; and a control unit electrically coupled to the first and second electrodes, wherein the control unit is configured to actuate the first and second electrodes to generate an electric field at the fracture; and one or more magnets disposed adjacent to the fracture, wherein the one or more magnets are configured to generate a magnetic field in a direction orthogonal to the electric field in order to drive interstitial fluid flow at the fracture.

Example 14. The assembly of any example herein, particularly example 13, wherein the bone fixation plate comprises an elongated main body and first and second extension members extending in a same direction from opposite sides of the main body such that the first and second extension members are spaced apart from one another.

Example 15. The assembly of any example herein, particularly example 14, wherein the first electrode is disposed on or in the first extension member and the second electrode is disposed on or in the second extension member, and wherein the first and second extension members extend from a central portion of the main body.

Example 16. The assembly of any example herein, particularly either example 14 or example 15, wherein the control unit is disposed on or in a central portion of the main body.

Example 17. The assembly of any example herein, particularly any one of examples 13-16, wherein the bone fixation plate comprises a plurality of apertures, each aperture configured to receive a fastener for fixing the bone fixation plate to the bone of the subject.

Example 18. The assembly of any example herein, particularly any one of examples 13-17, wherein the control unit comprises a microcontroller, a power supply or coil, a power regulator, relays which are configured to switch between sensing and stimulating modes, and a network analyzer which is configured to measure an impedance of the bone at the fracture, between the first and second electrodes, for determination of a status of the bone, wherein in the sensing mode a signal from the first and second electrodes provides feedback as to the status of bone at the fracture as it heals, and wherein in the stimulating mode the first and second electrodes supply the electric field for generating the interstitial fluid flow.

Example 19. The assembly of any example herein, particularly any one of examples 13-18, wherein the one or more magnets includes two magnets disposed on an outside of a body of the subject, adjacent to the fracture.

Example 20. The assembly of any example herein, particularly example 19, wherein the two magnets are spaced apart from one another on or in a wearable harness that is configured to be positioned around the body of the subject, at a region of the fracture of the bone to which the bone fixation implant is coupled.

In view of the many possible examples to which the principles of the disclosure may be applied, it should be recognized that the illustrated configurations depict examples of the disclosed technology and should not be taken as limiting the scope of the disclosure nor the claims. Rather, the scope of the claimed subject matter is defined by the following claims and their equivalents.

The invention claimed is:

1. An assembly for promoting interstitial fluid flow, comprising:

an implant configured to be disposed at a selected site of a subject, the implant comprising spaced apart first and second electrodes;

a control unit electrically coupled to the first and second electrodes, the control unit configured to provide power to the first and second electrodes to generate an electric field at the selected site, and measure an electrical impedance between the first and second electrodes; and one or more magnets disposed adjacent to the selected site, the one or more magnets configured to generate a magnetic field in a direction orthogonal to the electric field in order to drive interstitial fluid flow at the selected site at a specified flow rate and direction, and wherein the control unit is configured to adjust voltage applied to the first and second electrodes to adjust the electric field based on the measured electrical impedance to adjust the flow rate of the interstitial fluid flow.

2. The assembly of claim 1, wherein the selected site is a fracture in a subject's bone, wherein the implant and the control unit are implanted within the subject at the selected site, and wherein the implant is configured to be placed in contact with the subject's bone and span the fracture, with the first and second electrodes disposed on either side of the fracture.

3. The assembly of claim 1, wherein the one or more magnets are disposed in a wearable harness that is configured to be worn by the subject, external and adjacent to the selected site.

4. The assembly of claim 1, wherein the control unit is disposed on the implant.

5. The assembly of claim 1, wherein the control unit comprises a microcontroller, a power supply, and a power regulator, and wherein the control unit is connected to the first and second electrodes by wires.

6. The assembly of claim 5, wherein the control unit further comprises:

relays which are configured to switch between sensing and stimulating modes, wherein in the sensing mode a signal from the first and second electrodes provides feedback as to a status of a tissue at the selected site as it heals, and wherein in the stimulating mode the first and second electrodes supply the electric field for generating the interstitial fluid flow; and a network analyzer which is configured to measure the electrical impedance between the first and second electrodes, for determination of the status of the tissue.

7. The assembly of claim 1, wherein the one or more magnets includes a pair of magnets that are placed at a perpendicular orientation relative to the first and second electrodes.

8. A method of treating a subject in need thereof, comprising disposing the assembly of claim 1 at the selected site and generating the electric field orthogonal to the magnetic field at the selected site for a predetermined duration of time.

9. The method of claim 8, wherein generating the electric field comprises applying pulsed input voltage to the first and second electrodes for the predetermined duration of time at a non-50% on/off pulsed amplitude cycle.

10. The method of claim 8, wherein the subject has a bone fracture, a laceration, or a shallow tissue injury at the selected site.

11. The method of claim 8, wherein the predetermined duration of time is in a range of 15-25 minutes, and further comprising generating the electric field orthogonal to the magnetic field at the selected site for the predetermined duration of time starting at 14-21 days following implantation of the implant at the selected site and at a frequency of two to three times per week.

12. The method of claim 8, further comprising switching from a stimulating mode where the electric field is generated by the first and second electrodes to a sensing mode where a signal from the first and second electrodes is obtained by the control unit and processed to determine an impedance of a tissue at the selected site for a determination of a healing status of the tissue.

13. An assembly for promoting interstitial fluid flow, comprising:

a bone fixation implant comprising:

a bone fixation plate configured to be coupled to a bone of a subject at a location of a fracture;

first and second electrodes that are spaced apart from one another; and a control unit electrically coupled to the first and second electrodes, wherein the control unit is configured to actuate the first and second electrodes to generate an electric field at the fracture and adjust the generated electric field based on an electrical impedance measured between the first and second electrodes; and one or more magnets disposed adjacent to the fracture, wherein the one or more magnets are configured to generate a magnetic field in a direction orthogonal to the electric field in order to drive interstitial fluid flow at the fracture at a specified flow rate and direction for bone healing.

14. The assembly of claim 13, wherein the bone fixation plate comprises a plurality of apertures, each aperture configured to receive a fastener for fixing the bone fixation plate to the bone of the subject.

15. The assembly of claim 13, wherein the control unit comprises a microcontroller, a power supply or coil, a power regulator, relays which are configured to switch between sensing and stimulating modes, and a network analyzer which is configured to measure the electrical impedance of the bone at the fracture, between the first and second electrodes, for determination of a status of the bone, wherein in the sensing mode a signal from the first and second electrodes provides feedback as to the status of bone at the fracture as it heals, and wherein in the stimulating mode the first and second electrodes supply the electric field for generating the interstitial fluid flow at the specified flow rate and direction.

16. The assembly of claim 13, wherein the one or more magnets includes two magnets disposed on an outside of a body of the subject, adjacent to the fracture.

17. The assembly of claim 16, wherein the two magnets are spaced apart from one another on or in a wearable harness that is configured to be positioned around the body of the subject, at a region of the fracture of the bone to which the bone fixation implant is coupled.

18. An assembly for promoting interstitial fluid flow, comprising:

a bone fixation implant comprising:

a bone fixation plate configured to be coupled to a bone of a subject at a location of a fracture;

first and second electrodes that are spaced apart from one another; and a control unit electrically coupled to the first and second electrodes, wherein the control unit is configured to actuate the first and second electrodes to generate an electric field at the fracture; and one or more magnets disposed adjacent to the fracture, wherein the one or more magnets are configured to generate a magnetic field in a direction orthogonal to the electric field in order to drive interstitial fluid flow at the fracture, wherein the bone fixation plate comprises an elongated main body and first and second extension members extending in a same direction from opposite sides of the main body such that the first and second extension members are spaced apart from one another.

19. The assembly of claim 18, wherein the first electrode is disposed on or in the first extension member and the second electrode is disposed on or in the second extension member, and wherein the first and second extension members extend from a central portion of the main body.

20. The assembly of claim 18, wherein the control unit is disposed on or in a central portion of the main body.

* * * * *